(12) United States Patent
Musa

(10) Patent No.: US 8,946,367 B2
(45) Date of Patent: Feb. 3, 2015

(54) POLYMERIZABLE CARBAMATE AND THIOCARBAMATE COMPOUNDS, POLYMERS DERIVED FROM THEM, AND COMPOSITIONS THEREOF

(75) Inventor: Osama M. Musa, Kinnelon, NJ (US)

(73) Assignee: ISP Investments Inc., Wilmington, DE (US)

( * ) Notice: Subject to any disclaimer, the term of this patent is extended or adjusted under 35 U.S.C. 154(b) by 18 days.

(21) Appl. No.: 13/704,871

(22) PCT Filed: Jun. 22, 2011

(86) PCT No.: PCT/US2011/041375
§ 371 (c)(1),
(2), (4) Date: Dec. 17, 2012

(87) PCT Pub. No.: WO2011/163317
PCT Pub. Date: Dec. 29, 2011

(65) Prior Publication Data
US 2013/0090443 A1      Apr. 11, 2013

Related U.S. Application Data

(60) Provisional application No. 61/357,216, filed on Jun. 22, 2010.

(51) Int. Cl.
| | | |
|---|---|---|
| *C08F 8/34* | (2006.01) | |
| *C08F 228/02* | (2006.01) | |
| *C08F 226/08* | (2006.01) | |
| *C07C 333/04* | (2006.01) | |
| *A01N 25/24* | (2006.01) | |
| *A61Q 17/00* | (2006.01) | |
| *C08G 18/38* | (2006.01) | |
| *C08G 18/81* | (2006.01) | |
| *A61K 8/87* | (2006.01) | |
| *C07C 271/12* | (2006.01) | |
| *C08F 226/10* | (2006.01) | |
| *C08F 220/06* | (2006.01) | |
| *C08F 212/14* | (2006.01) | |
| *C08F 220/18* | (2006.01) | |
| *C08F 220/34* | (2006.01) | |

(52) U.S. Cl.
CPC .............. *C07C 333/04* (2013.01); *A01N 25/24* (2013.01); *A61Q 17/005* (2013.01); *C08G 18/3876* (2013.01); *C08G 18/8108* (2013.01); *A61K 8/87* (2013.01); *C07C 271/12* (2013.01); *C08F 226/10* (2013.01); *C08F 226/08* (2013.01); *C08F 220/06* (2013.01); *C08F 212/14* (2013.01); *C08F 2220/1883* (2013.01); *C08F 220/34* (2013.01)

USPC .......................................... 526/301; 526/288

(58) Field of Classification Search
CPC ... C07C 333/04; C07C 271/12; C08F 226/10; C08F 212/14; C08F 220/34; C08F 220/06; C08F 2220/1883; C08G 18/8108; C08G 18/3876
USPC .................................................. 526/301, 288
See application file for complete search history.

(56) References Cited

U.S. PATENT DOCUMENTS

| | | |
|---|---|---|
| 2004/0224109 A1 | 11/2004 | Lynch et al. |
| 2007/0148121 A1* | 6/2007 | Fukui et al. ................. 424/70.16 |
| 2008/0143958 A1 | 6/2008 | Medina et al. |
| 2009/0208719 A1* | 8/2009 | Kang et al. ..................... 428/220 |

FOREIGN PATENT DOCUMENTS

| | | | |
|---|---|---|---|
| JP | 2005105002 A | * | 4/2005 |
| JP | 2009269866 A | * | 11/2009 |
| WO | WO 01/23484 | | 4/2001 |
| WO | WO 2007148684 A1 | * | 12/2007 |

OTHER PUBLICATIONS

International Search Report, PCT/US2011/041375, published on Dec. 29, 2011.

* cited by examiner

*Primary Examiner* — Ling Choi
*Assistant Examiner* — David L Miller
(74) *Attorney, Agent, or Firm* — William J. Davis

(57) ABSTRACT

Carbamate and thiocarbamate compounds are described that comprise a polymerizable moiety and one or more free hydroxyl and/or thiol groups. Polymers may be obtained by polymerizing these carbamate and/or thiocarbamate compounds. The carbamate and thiocarbamate compounds, as well as the polymers they produce may be formulated into adhesive, agricultural, biocide, cleaning, coating, encapsulation, membrane, oilfield, performance chemical, and personal care compositions.

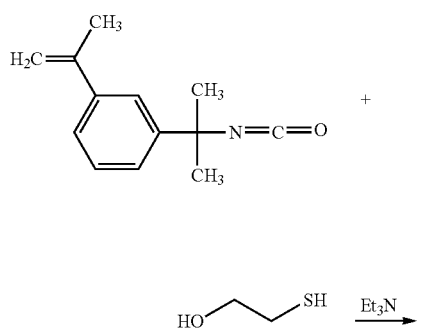

-continued
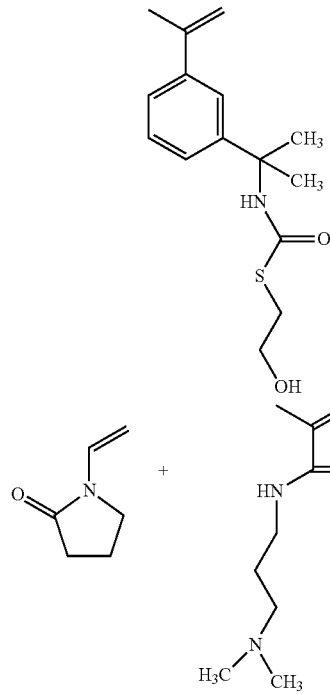
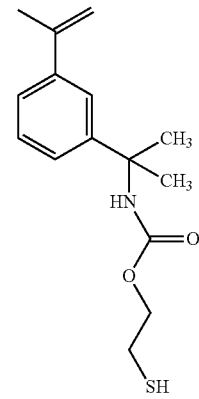
-continued
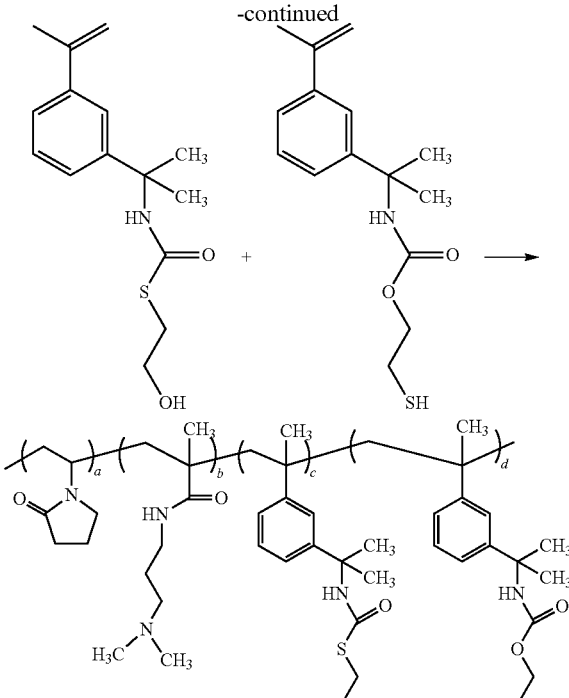
2 Claims, No Drawings

POLYMERIZABLE CARBAMATE AND THIOCARBAMATE COMPOUNDS, POLYMERS DERIVED FROM THEM, AND COMPOSITIONS THEREOF

CROSS-REFERENCE

This application is the national stage of PCT Application No. PCT/US2011/041375 filed June 22, 2011 which claims priority of the provisional application number 61/357,216 filed June 22, 2010, the entire disclosures of which are hereby incorporated in their entirety.

BACKGROUND OF THE INVENTION

1. Field of the Invention

Provided herein are carbamate and thiocarbamate compounds having a polymerizable moiety and one or more free hydroxyl and/or thiol groups. The invention further relates to polymers obtained from the abovementioned compounds, as well as compositions thereof.

2. Description of Related Art

Several catalyzed and uncatalyzed reactions between an isocyanate-containing compound, such as p-methoxyphenyl isocyanate, benzyl isocyanate or 1-naphthyl isocyanate, and 2-mercaptoethanol resulting in the formation of carbamate and thiocarbamate addition products are known and described by Smith et al. in *Journal of American Chemical Society*, 1959, 81 (1), pages 161-163.

The kinetics of tertiary amine catalyzed reaction of organic isocyanates with thiols is described by Iwakura et al. in *Canadian Journal of Chemistry*, 1960, 38, pages 2418-2424. The study involved tertiary amine as a catalyst and a mechanism was proposed for the reaction of phenyl isocyanate with 1-butanethiol in toluene solution at 25° C.

The kinetics of triethylamine- and triethylenediamine-catalyzed reaction of phenyl isocyanate with 2-ethylhexanol, phenol, and hexanethiol in benzene at 25° C. are described by Farkas et al. in *Industrial & Engineering Chemistry Fundamentals*, 1965, 4(1), pages 32-38.

The rates of reaction of a group of phenyl-substituted isocyanates (phenyl isocyanate, nm-toluene diisocyanate and p,p'-diisocyanatodiphenylmethane) and a group of benzyl-substituted isocyanates (benzyl isocyanate, 1,3-xylene diisocyanate, 1,4-xylene diisocyanate and 5-t-butyl-1,3-xylene diisocyanate) with ethanol are described by Ferstanding et al. in *Journal of American Chemical Society*, 1959, 81(18), pages 4838-4842.

U.S. Pat. No. 7,339,020 discloses a process for preparing high-functionality polyisocyanates that have at least three free isocyanate groups and no free isocyanate reactive groups.

U.S. Pat. No. 5,451,695, which is hereby incorporated in its entirety by reference, discloses a polymerizable monomer useful as a starting material for producing high hardness transparent resins. One of the disclosed monomers has the structure:

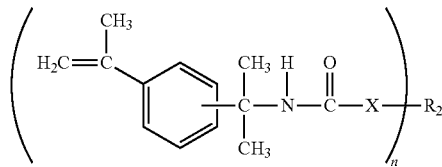

wherein X is selected from the group consisting of oxygen and sulfur, $R_2$ is selected from the group consisting of a saturated aliphatic residue having or not having at least one member selected from the group consisting of a halogen atom, an oxygen atom, an alicyclic ring, an heterocyclic ring and an aromatic ring, an alicyclic residue, and a heterocyclic residue, n is integer of 1-4. The '695 patent discloses the optional use of a urethane-forming accelerating catalyst such as dibutyl tin diisocyanate.

Several methods exist in literature for the synthesis of carbamates and thiocarbamates by the reaction of isocyanate compounds with compounds containing hydroxyl and/or thiol groups. These methods result in adducts that are devoid of free hydroxyl and/or thiol group(s). Further, polymerizable carbamates and thiocarbamates having free hydroxyl and/or thiol group(s) are expected to have diverse physicochemical properties that can be tailored to meet specific requirements. Therefore, there is a need to develop polymerizable carbamate and thiocarbamate compounds having one or more free hydroxyl and/or thiol groups.

SUMMARY OF THE INVENTION

Described herein are carbamate and thiocarbamate compounds having a polymerizable moiety and one or more free hydroxyl and/or thiol groups. Also described are polymers obtained from them, compositions comprising the novel carbamate/thiocarbamate compounds, compositions comprising the polymers obtained from them, as well as their uses.

DETAILED DESCRIPTION

As used in the specification and claims of this application, the following definitions are applicable.

The term "monomer" refers to a repeating structural unit of a polymer. A monomer is typically a low molecular weight compound that can form covalent chemical bonds with other monomers, resulting in a polymer.

The term "polymer" refers to a compound comprising repeating structural units (monomers) connected by covalent chemical bonds. The definition includes oligomers. Polymers may be further derivatized (for example by hydrolysis), crosslinked, grafted or end-capped. Non-limiting examples of polymers include homopolymers, non-homopolymers, block copolymers, terpolymers, quaternary polymers, and homologues. A polymer may be a random, block, or an alternating polymer, or a polymer with a mixed random, block, and/or alternating structure. Polymers may further be associated with solvent adducts.

The term "solvent adduct" refers to a solvent molecule that is bonded to a compound such as a polymer by one or more covalent bonds, ionic bonds, hydrogen bonds, coordinate covalent bonds, and/or Van der Waals forces of attraction.

The term "homopolymer" refers to a polymer consisting essentially of a single type of repeating structural unit (monomer). The definition includes homopolymers with solvent adducts.

The term "non-homopolymer" refers to a polymer having more than one type of repeating structural units (monomers). The definition includes non-homopolymers with solvent adducts.

The term "copolymer" refers to a non-homopolymer consisting essentially of two types of repeating structural units (monomers). The definition includes copolymers having solvent adducts.

The term "terpolymer" refers to a non-homopolymer consisting essentially of three types of repeating structural units (monomers). The definition includes terpolymers having solvent adducts.

The term "tetramer" refers to a non-homopolymer consisting essentially of four types of repeating structural units (monomers). The definition includes tetramers having solvent adducts.

The term "allyls" refers to moieties comprising at least one allyl group.

The term "styrenes" refers to any moieties comprising at least one styrene group. Non-limiting examples of styrenes includes α-methyl styrenes and β-methyl styrenes.

The α-methyl styrene structure represented as:

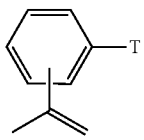

indicates the isopropenyl group can be attached at the meta, ortho, or para positions on the aromatic ring relative to T, which can be any group.

The term "branched" refers to any non-linear molecular structure. To avoid any arbitrary delineation, the term "branched" describes both branched and hyper branched structures.

The term "free radical addition polymerization initiator" refers to a compound used in a catalytic amount to initiate a free radical addition polymerization. The choice of an initiator depends mainly on its solubility and decomposition temperature.

The term "hetero atom" refers to an atom other than carbon such as oxygen, nitrogen, sulfur, or phosphorus.

The term "halogen" refers to chloro, bromo, iodo or fluoro.

The term "personal care composition" refers to a composition intended for use on or in the human body such as: oral care composition, hair care composition, face care composition, lip care composition, eye care composition, foot care composition, nail care composition, sun care composition, deodorant composition, antiperspirant composition, cosmetic composition (including color cosmetics), skin cleaning composition, insect repellant composition, shaving composition, and hygiene composition. Among their many uses, personal care compositions find application in enhancing hair shine, enhancing hair manageability, modulating hair stylability, protecting hair from thermal damage, repairing split ends, imparting humidity resistance to hair and hair styles, promoting hair style durability, changing the hair color, straightening and/or relaxing hair, providing protection from UV-A and/or UV-B radiation, imparting water resistance or water proofness, moisturizing skin, decreasing and/or minimizing the appearance of wrinkles, firming skin, decreasing or minimizing the appearance of skin blemishes (such as lentigo, skin discolorations, pimples, or acne), changing skin color (such as color cosmetics for the face, cheeks, eyelids, or eye lashes), and delivering an active (such as to the skin, hair, or oral cavity).

The term "performance chemicals composition" refers to compositions that are not personal care compositions. Performance chemicals compositions serve a broad variety of applications, non-limiting examples of which include: adhesives, agricultural, biocides, veterinary, coatings, electronics, household-industrial-institutional (HI&I), inks, membranes, metal fluids, oilfield, paper, paints, plastics, printing, plasters, textiles, fuels, lubricants, home care, and wood care compositions.

The term "(meth)acrylates" includes both acrylates and methacrylates. Analogously, the term "(meth)acrylamides" includes acrylamides and methacrylamides.

The term "functionalized and unfunctionalized alkyl, cycloalkyl, alkenyl, and aryl groups" refers to each of the alkyl, cycloalkyl, alkenyl, and aryl groups that may be substituted or unsubstituted. The substituted or unsubstituted groups may further contain one or more hetero atoms and/or halogen atoms. The alkyl and alkenyl groups may be branched or unbranched (straight-chain). In one embodiment, the alkyl and alkenyl groups are $C_1$-$C_{60}$, more particularly $C_1$-$C_{36}$, and most particularly $C_1$-$C_{18}$ groups. Cycloalkyls include cyclopentane, cyclohexane, cycloheptane, and the like. Aryl groups include benzene, naphthalene, anthracene, and the like, and heteroaryl groups such as pyridine, imidazole, and the like.

All percentages, ratios, and proportions used herein are on weight basis unless otherwise specified.

It has been discovered that compounds having at least one carbamate or thiocarbamate group, and at least one free hydroxyl and/or thiol group can be synthesized by reacting a first reactant having at least one isocyanate group, with a second reactant having at least two groups independently selected from the group consisting of hydroxyl and thiol groups and combinations thereof, being reacted with or without the presence of a catalyst.

In one aspect, the invention provides compounds represented by the structure:

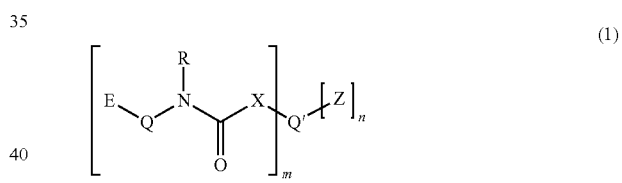

(1)

wherein:

each E is a polymerizable moiety independently selected from the group consisting of: (meth)acrylamides, (meth)acrylates, allyls, cinnamyls, fumarates, maleates, maleimides, α,β-olefinically unsaturated carboxylic nitriles, styrenes, vinyl esters, vinyl acetates, vinyl amides, vinyl alcohols, vinyl carbonates, vinyl carbamates, vinyl thiocarbamates, vinyl ureas, vinyl ethers, vinyl halides, vinyl imidazoles, vinyl lactams, vinyl pyridines, vinyl silanes, vinyl sulfones, benzoxazines, epoxies, oxazolines, oxetanes, and combinations thereof;

m and n1 are independently selected integers having a value of 1-5;

each Q and Q' is independently selected from the group consisting of functionalized and unfunctionalized alkylene of linear, branched, or cyclic structure and combinations thereof, wherein any of the beforementioned groups may be with or without heteroatoms;

each R is independently selected from the group consisting of hydrogen, functionalized and unfunctionalized alkyl, cycloalkyl, alkenyl, and aryl groups, wherein any of the beforementioned groups may be with or without heteroatoms;

each —X— is independently selected from the group consisting of —O—, —S—, and combinations thereof; and each —Z is independently selected from the group consisting of —OH, —SH and combinations thereof.

In another aspect, the invention provides compounds represented by the structure:

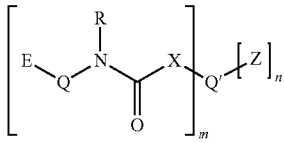

wherein:
each E is a polymerizable moiety independently selected from the group consisting of: (meth)acrylates, styrenes, and combinations thereof; m and n are independently selected integers having a value of 1-5;
each Q and Q' is independently selected from the group consisting of functionalized and unfunctionalized alkylene of linear, branched, or cyclic structure and combinations thereof, wherein any of the beforementioned groups may be with or without heteroatoms;
each R is independently selected from the group consisting of hydrogen, functionalized and unfunctionalized alkyl, cycloalkyl, alkenyl, and aryl groups, wherein any of the beforementioned groups may be with or without heteroatoms;
each —X— is independently selected from the group consisting of —O—, —S—, and combinations thereof; and
each —Z is independently selected from the group consisting of —OH, —SH and combinations thereof.

In another aspect, the invention provides compounds represented by the structure:

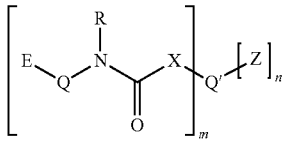

wherein:
each E is a polymerizable moiety independently selected from the group consisting of: (meth)acrylates, styrenes, and combinations thereof; m and n are independently selected integers having a value of 1-5;
each Q and Q' is independently selected from the group consisting of functionalized and unfunctionalized alkylene of linear, branched, or cyclic structure and combinations thereof, wherein any of the beforementioned groups may be with or without heteroatoms;
each R is hydrogen;
each —X— is independently selected from the group consisting of —O—, —S—, and combinations thereof; and
each —Z is independently selected from the group consisting of —OH, —SH and combinations thereof.

In the aspects set forth for the invention, the valence of Q' is equal to the sum of the integral values of m and n. Hence, the minimum valence of Q' is 2, when both m and n are equal to 1.

In yet another aspect, the invention provides compounds represented by the structure:

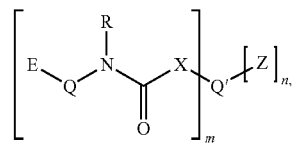

wherein:
each E is a polymerizable moiety independently selected from the group consisting of: (meth)acrylates, styrenes, and combinations thereof;
m and n are each 1;
each Q and Q' is independently selected from the group consisting of functionalized and unfunctionalized alkylene of linear, branched, or cyclic structure and combinations thereof, wherein any of the beforementioned groups may be with or without heteroatoms;
each R is hydrogen;
each —X— is independently selected from the group consisting of —O—, —S—, and combinations thereof; and
each —Z is independently selected from the group consisting of —OH, —SH and combinations thereof.

The polymerizable moiety E may be selected from the group consisting of styrene, α-methyl styrene, acrylate, methacrylate, and combinations thereof.

A compound with α-methyl styrene as the polymerizable moiety E can be represented by the structure:

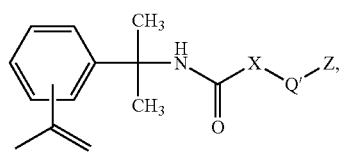

wherein:
Q' is selected from the group consisting of functionalized and unfunctionalized alkylene of linear, branched, or cyclic structure and combinations thereof, wherein any of the beforementioned groups may be with or without heteroatoms;
—X— is —O— or —S—; and
—Z is —OH or —SH.

As represented in the above α-methyl styrene structure, the point of attachment of the isopropenyl group on the aromatic ring can be ortho-, meta- or para-. In one embodiment, the point of attachment is meta-. In a separate embodiment, Q' can be an alkylene group represented by the structure —$(CH_2)_k$—, wherein k is an integer equal to or greater than 1; optionally, one or more hydrogen atom in —$(CH_2)_k$— is independently substituted by one or more halogen atoms, C1-C5 alkyl, amino, hydroxyl or alkoxy groups, or combinations thereof; and optionally, one or more —$CH_2$— in —$(CH_2)_k$— is independently replaced by one or more —O—, —S—, or —$N(R_1)$—. In accordance with certain aspects, Q' has the structure: —$CH_2$—$CH_2$—.

When the polymerizable moiety E is α-methyl styrene, then a compound can be represented by the structure:

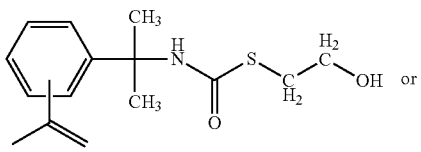

or

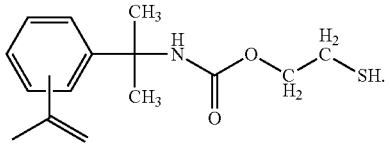

As represented in the above structure, the point of attachment of the isopropenyl group on the aromatic ring can be ortho-, meta- or para-. As suggested above, the point of attachment can be meta-.

In addition to α-methyl styrenes, other polymerizable moieties E can be used. For example, a compound with (meth)acrylate as the polymerizable moiety E can have the structure:

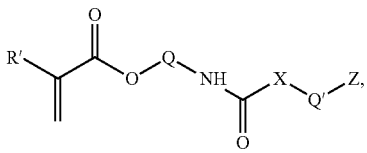

wherein:

R' is hydrogen or methyl;

Q and Q' is each independently selected from the group consisting of functionalized and unfunctionalized alkylene of linear, branched, or cyclic structure and combinations thereof, wherein any of the beforementioned groups may be with or without heteroatoms;

—X— is —O— or —S—; and

—Z is —OH or —SH.

In a separate embodiment for the structure immediately shown above, each Q and Q' can be independently selected from an alkylene group represented by the structure —$(CH_2)_k$—, wherein k is an integer equal to or greater than 1; optionally, one or more hydrogen atom in —$(CH_2)_k$— is independently substituted by one or more halogen atoms, C1-C5 alkyl, amino, hydroxyl or alkoxy groups, or combinations thereof; and optionally, one or more —$CH_2$— in —$(CH_2)_k$— is independently replaced by one or more —O—, —S—, or —N($R_1$)—. As a non-limiting illustration, each Q and Q' may have the structure: —$CH_2$—$CH_2$—.

Further examples of this embodiment include a compound with (meth)acrylate as the polymerizable moiety E can be represented by the structure:

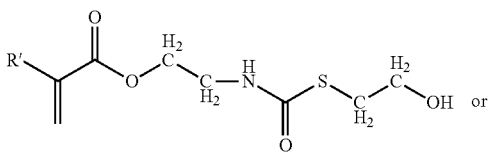

or

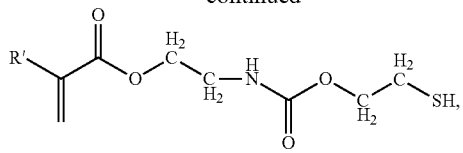

wherein each R' is independently hydrogen or methyl.

Still other polymerizable moieties E may be employed. In a non-limiting example, a polymerizable acrylate moiety E according to the invention has the structure:

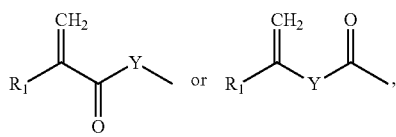

wherein —Y— is —O— or —N($R_1$)—, and each $R_1$ is independently selected from the group consisting of hydrogen, functionalized alkyl and unfunctionalized alkyl.

In a non-limiting example, a polymerizable vinyl lactam moiety E according to the invention is selected from the group consisting of N-vinyl lactams, C-vinyl lactams, and derivatives thereof.

The N-vinyl lactams have the structure:

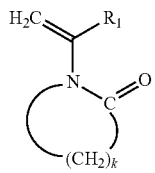

wherein $R_1$ is selected from the group consisting of hydrogen, functionalized alkyl and unfunctionalized alkyl; k is an integer equal to or greater than 1; optionally, one or more hydrogen atoms in —$(CH_2)_k$— are independently substituted by one or more halogen atoms, $C_1$-$C_5$ alkyl, amino, hydroxyl or alkoxy groups, or combinations thereof; and optionally, one or more —$CH_2$— in —$(CH_2)_k$— is independently replaced by one or more —O—, —S—, or —N($R_2$)—. $R_2$ is selected from the group consisting of hydrogen, functionalized alkyl and unfunctionalized alkyl. In a particular embodiment, k is equal to 3 or 5 resulting in a pyrrolidone and caprolactam, respectively.

The C-vinyl lactams have the structure:

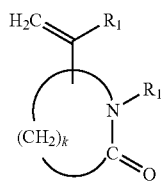

wherein each $R_1$ is selected from the group consisting of hydrogen, functionalized alkyl and unfunctionalized alkyl; k is an integer greater than 1; optionally, one or more hydrogen atoms in —$(CH_2)_k$— are independently substituted by one or more halogen atoms, $C_1$-$C_5$ alkyl, amino, hydroxyl or alkoxy groups, or combinations thereof; and optionally, one or more —$CH_2$— in —$(CH_2)_k$— is independently replaced by one or more —O—, —S—, or —$N(R_2)$—. $R_2$ is selected from the group consisting of hydrogen, functionalized alkyl and unfunctionalized alkyl. In a particular embodiment, k is equal to 3 or 5 resulting in a pyrrolidone and caprolactam respectively.

In a non-limiting example, a polymerizable fumarate or maleate moiety E according to the invention has the structure:

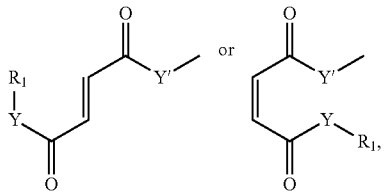

wherein —Y— and —Y'— are independently selected from the group consisting of —O— and —$N(R_1)$—, and each $R_1$ is independently selected from the group consisting of hydrogen, functionalized alkyl and unfunctionalized alkyl. Each $R_1$ can be independently selected from the group consisting of hydrogen and methyl.

In a non-limiting example, a polymerizable vinyl ether moiety E according to the invention has the structure:

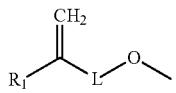

wherein $R_1$ is selected from the group consisting of hydrogen, functionalized alkyl and unfunctionalized alkyl; -L- is either a direct bond connecting the carbon and oxygen, or -L- has the structure —$(CH_2)_k$—, wherein k is an integer equal to or greater than 1; optionally, one or more hydrogen atoms in —$(CH_2)_k$— are independently substituted by one or more halogen atoms, $C_1$-$C_5$ alkyl, amino, hydroxyl or alkoxy groups, or combinations thereof; and optionally, one or more —$CH_2$— in —$(CH_2)_k$— is independently replaced by one or more —O—, —S—, or —$N(R_2)$—. $R_2$ is selected from the group consisting of hydrogen, functionalized alkyl and unfunctionalized alkyl. For example, $R_2$ can be selected from the group consisting of hydrogen and methyl.

The compounds according to the invention belong to the class of carbamates (when —X— is —O—) and thiocarbamates (when —X— is —S—).

Compounds represented by structure (1) can be synthesized from at least one isocyanate compound as the first reactant and at least one second reactant having one or more hydroxyl and/or thiol groups.

In one aspect, this second reactant can be represented by the structure:

$$[HX]_i{=}Q'{=}[Z]_j$$

wherein:
i and j are independently selected integers having a value of 1-5;
Q' is selected from the group consisting of functionalized and unfunctionalized alkylene of linear, branched, or cyclic structure and combinations thereof, wherein any of the beforementioned groups may be with or without heteroatoms;

each —X— is independently selected from the group consisting of —O— and —S—;
H is a hydrogen atom; and
each —Z is independently selected from the group consisting of —OH and —SH.

Non-limiting examples of this second reactant include ethylene glycol, 1,3-propanediol, 1,4-butanediol, 1,4-butenediol, 1,5-pentanediol, 1,6-hexanediol, 1,2-propanediol, 1,3-butanediol, 2,3-butanediol, 2,5-hexanediol, diethylene glycol, neopentyl glycol, 3-methyl-1,5-pentanediol, dipropylene glycol, triethylene glycol, 1,2-butanediol, 2-ethyl-1,3-hexanediol, spiroglycol, 1,4-cyclohexanediol, tricyclo[5,2,1,0.sup.2,6]decane-4,8-dimethanol, 3-chloro-1,2-propanediol, 3-bromo-1,2-propanediol, 2,3-dibromo-1,4-butanediol, dibromoneopentylglycol, bisphenol A (2-hydroxyethyl) ether, bisphenol F (2-hydroxyethyl)ether, bisphenol S (2-hydroxyethyl)ether, biphenol(2-hydroxyethyl)ether, tetrabromo bisphenol A (2-hydroxyethyl)ether, benzene dimethanol, ethanedithiol, propanedithiol, butanedithiol, pentanedithiol, hexanedithiol, propanetrithiol, cyclohexanedithiol, ethylene glycol bis(2-mercaptoacetate), ethylene glycol bis(3-mercaptopropionate), bis(mercaptomethyl)benzene, 2-hydroxy ethyl disulfide, 2-mercaptoethanol, 1-mercapto-2-propanol, glycerol, trimethylolethane, trimethylolpropane, 1,2,4-butanetriol, 1,2,6-hexanetriol, 1,3,5-tris(2-hydroxyethyl)cyanuric acid, pentaerythritol, threitol, 3-mercapto-1,2-propanediol, pentaerythritol tetrakis(2-mercaptoacetate) and pentaerythritol tetrakis(3-mercaptopropionate).

The reaction comprising the first and second reactants may be performed with or without added catalyst(s). The chemist may chose to perform the reaction in the presence of an organometallic or a tertiary amine or compound as a catalyst.

Non-limiting examples of organometallic compounds that may be used as catalysts include dibutyltin diisocyanate, bis (tri-n-alkyl tin)oxide, dialkyltin dicarboxylate, dibutyltin diacetate, dibutyltin dilaurate, dibutyltin di(2-ethylhexanoate), bismuth tris(2-ethylhexanoate) and zirconium tetrakis(2,4-pentanedionato).

Non-limiting examples of tertiary amines that may be used as catalysts include trimethyl amine, triethyl amine, triethylene diamine, diethylcyclohexyl amine, tributyl amine, N-alkylmorpholine, pyridine, quinoline, trioctylamine, N,N-dimethyl-n-octylamine, N,N-dimethyl-n-dodecylamine, N,N-dimethyl-n-hexadecylamine and the respective N,N-diethyl or N-methyl-N-ethyl compounds, and 1,4-diazabicyclo [2,2,2]-octane.

An example of a tertiary amine catalyst is triethyl amine.

With the discovery of polymerizable carbamate and thiocarbamate compounds having at least one free hydroxyl and/or thiol group, the invention also provides for polymers made from them. For example, homopolymers may be prepared by polymerizing a monomer represented by the structure:

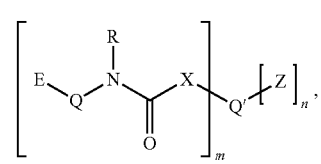

wherein:
each E is a polymerizable moiety independently selected from the group consisting of: (meth)acrylamides, (mneth) acrylates, allyls, cinnamyls, fumarates, maleates, maleimides, α,β-olefinically unsaturated carboxylic nitriles, styrenes, vinyl esters, vinyl acetates, vinyl amides, vinyl alcohols, vinyl carbonates, vinyl carbamates, vinyl thiocarbamates, vinyl ureas, vinyl ethers, vinyl halides, vinyl imidazoles, vinyl lactams, vinyl pyridines, vinyl silanes, vinyl sulfones, benzoxazines, epoxies, oxazolines, oxetanes, and combinations thereof;

m and n are independently selected integers having a value of 1-5;

each Q and Q' is independently selected from the group consisting of functionalized and unfunctionalized alkylene of linear, branched, or cyclic structure and combinations thereof, wherein any of the beforementioned groups may be with or without heteroatoms;

each R is independently selected from the group consisting of hydrogen, functionalized and unfunctionalized alkyl, cycloalkyl, alkenyl, and aryl groups, wherein any of the beforementioned groups may be with or without heteroatoms;

each —X— is independently selected from the group consisting of —O—, —S—, and combinations thereof; and each —Z is independently selected from the group consisting of —OH, —SH and combinations thereof.

The weight-average molecular weight of homopolymers embraced by the invention may range from about 500 Da to about 20,000,000 Da or more. In one embodiment, the molecular weight ranges from about 1,000 Da to about 10,000,000 Da. For other embodiments, the molecular weight ranges from about 2,000 Da to about 5,000,000 Da. A polymer scientist skilled in the art understands how to judiciously select reaction conditions and reactants, such as the type(s) and amount(s) of monomer(s), initiator(s) and/or chain transfer agent(s) (if any), to achieve these molecular weights. The choice of non-reactive solvent(s) may assist in achieving a desired molecular weight. The polymer scientist also may elect a particular polymerization method, such as free radical, anionic, cationic, emulsion, or suspension, to produce a target molecular weight. A reference on these methods is *Introduction to Polymers* by R. J. Young (CRC Press, second edition, ISBN: 978-0748757404), which is incorporated herein its entirety by reference.

As one skilled in the art will appreciate, compounds having an α-alkyl styrene group, such as the m-TMI-ME monomer (an illustration of which is provided in Example 1), may require special homopolymerization methods, which also are embraced by the present invention. These methods include those described in U.S. Pat. No. 4,891,441 and EP 130,313, each of which is hereby incorporated in its entirety by reference.

In accordance with one aspect, the invention provides homopolymers consisting essentially of polymers based on the above polymerizable compound wherein E is an α-alkyl styrene group. One such homopolymer is prepared by polymerizing a monomer represented by the structure:

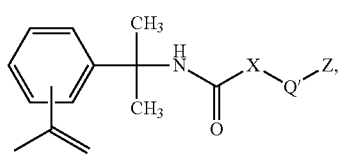

wherein:
Q' is selected from the group consisting of functionalized and unfunctionalized alkylene of linear, branched, or cyclic structure and combinations thereof, wherein any of the beforementioned groups may be with or without heteroatoms;

—X— is —O— or —S—; and
—Z is —OH or —SH.

More specifically, the homopolymer may be prepared by polymerizing a monomer represented by the structure:

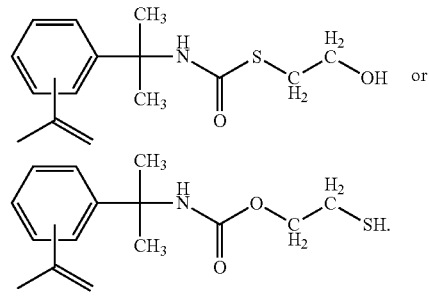

In another aspect, the invention provides homopolymers that can be synthesized from monomers represented by structure (1) wherein E is (meth)acrylate group. One such homopolymer consists essentially of repeating units upon the polymerization of a compound represented by the structure:

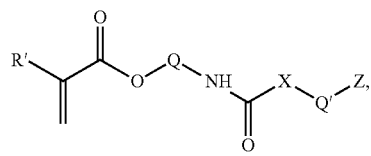

wherein:
R' is hydrogen or methyl;
each Q and Q' is independently selected from the group consisting of functionalized and unfunctionalized alkylene of linear, branched, or cyclic structure and combinations thereof, wherein any of the beforementioned groups may be with or without heteroatoms;
—X— is —O— or —S—; and
—Z is —OH or —SH.

As one illustration of this embodiment, the homopolymer may be polymerized using a monomer represented by the structure:

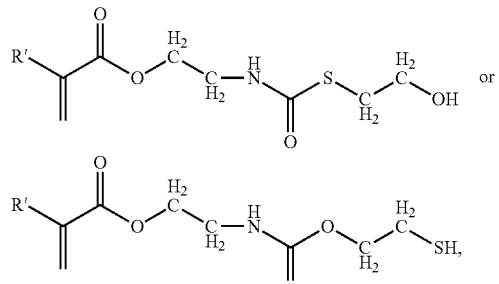

wherein: R' is hydrogen or methyl.

The homopolymers according to the invention may be further associated with solvent adducts.

Similarly, the invention also provides a vast array of non-homopolymers that can be polymerized from at least a first monomer that can be represented by the structure:

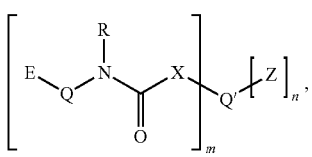

and at least one second monomer different from the first monomer,
wherein:
each E is a polymerizable moiety independently selected from the group consisting of: (meth)acrylamides, (meth)acrylates, allyls, cinnamyls, fumarates, maleates, maleimides, $\alpha,\beta$-olefinically unsaturated carboxylic nitriles, styrenes, vinyl esters, vinyl acetates, vinyl amides, vinyl alcohols, vinyl carbonates, vinyl carbamates, vinyl thiocarbamates, vinyl ureas, vinyl ethers, vinyl halides, vinyl imidazoles, vinyl lactams, vinyl pyridines, vinyl silanes, vinyl sulfones, benzoxazines, epoxies, oxazolines, oxetanes, and combinations thereof;
m and n are independently selected integers having a value of 1-5;
each Q and Q' is independently selected from the group consisting of fimunctionalized and unfunctionalized alkylene of linear, branched, or cyclic structure and combinations thereof, wherein any of the beforementioned groups may be with or without heteroatoms;
each R is independently selected from the group consisting of hydrogen, functionalized and unfunctionalized alkyl, cycloalkyl, alkenyl, and aryl groups, wherein any of the beforementioned groups may be with or without heteroatoms;
each —X— is independently selected from the group consisting of —O—, —S—, and combinations thereof; and
each —Z is independently selected from the group consisting of —OH, —SH and combinations thereof.

The at least one second monomer may be selected from the group consisting of: (meth)acrylamides, (meth)acrylates, allyls, benzoxanes, cinnamyls, epoxies, fumarates, maleates, maleimides, $\alpha,\beta$-olefinically unsaturated carboxylic nitriles, oxazolines, oxetanes, styrenes, vinyl esters, vinyl acetates, vinyl amides, vinyl alcohols, vinyl carbonates, vinyl carbamates, vinyl thiocarbamates, vinyl ureas, vinyl ethers, vinyl halides, vinyl imidazoles, vinyl lactams, vinyl pyridines, vinyl silanes, vinyl sulfones, derivatives thereof, and blends thereof.

In one embodiment, the at least one second monomer is selected from the group consisting of: N-vinyl-2-pyrrolidone, N-vinyl-2-caprolactam, acrylic acid, acrylate salts, methacrylic acid, methacrylate salts, acrylamide, methacrylamide, dimethylaminopropyl methacrylamide, dimethylaminopropyl methacrylate, lauryl methacrylate, dimethylaminopropyl acrylamide, dimethylaminopropyl acrylate, lauryl acrylate, m-isopropenyl-$\alpha,\alpha$-dimethylbenzyl isocyanate, 2-acrylamido-2-methylpropane sulfonic acid (AMPS), salts of AMPS, derivatives thereof, and blends thereof.

As with the homopolymers, the weight-average molecular weight of non-homopolymers embraced by the invention may range from about 500 Da to about 20,000,000 Da or more. In one embodiment, the molecular weight ranges from about 1,000 Da to about 10,000,000 Da. For other embodiments, the molecular weight ranges from about 2,000 Da to about 5,000,000 Da.

The non-homopolymers according to the invention are alternating, random, graft, or block non-homopolymers. It is also possible that the non-homopolymers have a mixed alternating, random, graft, and/or block structure. The non-homopolymers may be further end-capped or derivatized by methods known in the art.

The non-homopolymers according to the invention may be further associated with solvent adducts.

Non-limiting examples of non-homopolymers include copolymers, terpolymers and tetramers.

The non-homopolymers according to the invention comprise from about 0.001 mole percent to about 99.999 mole percent of the first monomer, and from about 0.001 mole percent to about 99.999 mole percent of other monomers. The sum of all monomers in the non-homopolymer is 100 mole percent.

In one aspect, the invention provides a non-homopolymer that is synthesized by polymerizing a first monomer represented by the structure:

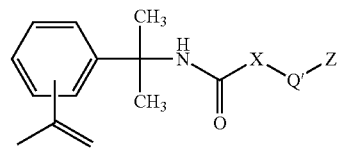

and at least one second monomer different from the first monomer,
wherein:
Q' is selected from the group consisting of functionalized and unfunctionalized alkylene of linear, branched, or cyclic structure and combinations thereof, wherein any of the beforementioned groups may be with or without heteroatoms;
—X— is —O— or —S—; and
—Z is —OH or —SH.

The at least one second monomer may be selected from the group consisting of: (meth)acrylamides, (meth)acrylates, allyls, benzoxanes, cinnamyls, epoxies, fumarates, maleates, maleimides, $\alpha,\beta$-olefinically unsaturated carboxylic nitriles, oxazolines, oxetanes, styrenes, vinyl esters, vinyl acetates, vinyl amides, vinyl alcohols, vinyl carbonates, vinyl carbamates, vinyl thiocarbamates, vinyl ureas, vinyl ethers, vinyl halides, vinyl imidazoles, vinyl lactams, vinyl pyridines, vinyl silanes, vinyl sulfones, derivatives thereof, and blends thereof. In one particular embodiment, the at least one second monomer is selected from the group consisting of: N-vinyl-2-pyrrolidone, N-vinyl-2-caprolactam, acrylic acid, acrylate salts, methacrylic acid, methacrylate salts, acrylamide, methacrylamide, dimethylaminopropyl methacrylamide, dimethylaminopropyl methacrylate, lauryl methacrylate, dimethylaminopropyl acrylamide, dimethylaminopropyl acrylate, lauryl acrylate, m-isopropenyl-$\alpha,\alpha$-dimethylbenzyl isocyanate, 2-acrylamido-2-methylpropane sulfonic acid (AMPS), salts of AMPS, derivatives thereof, and blends thereof.

In a particular embodiment of this aspect of the invention, the non-homopolymer is synthesized by polymerizing a first monomer represented by the structure:

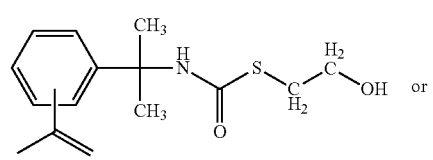

or

-continued

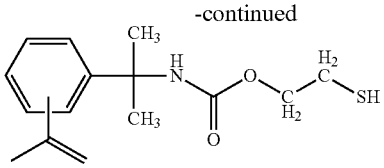

with at least one second monomer as defined in the immediate above paragraph.

In yet another aspect, the invention provides a non-homopolymer that is synthesized by polymerizing a first monomer represented by the structure:

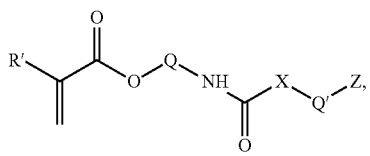

and at least one second monomer,
wherein:
R' is hydrogen or methyl;
each Q and Q' is independently selected from the group consisting of functionalized and unfunctionalized alkylene of linear, branched, or cyclic structure and combinations thereof, wherein any of the beforementioned groups may be with or without heteroatoms;
—X— is —O— or —S—; and
—Z is —OH or —SH.

For example, one non-homopolymer can be represented by the structure:

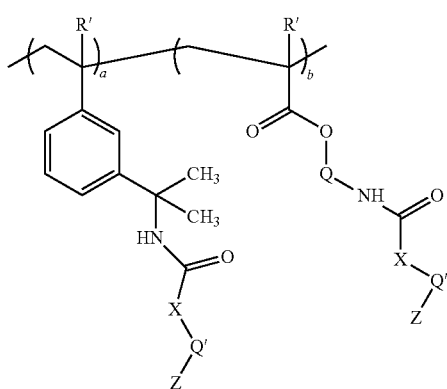

wherein:
a, and b are molar percentages wherein each ranges from about 0.001 mole percent to about 99.999 mole percent, and wherein the sum of said molar percentages for any non-homopolymer is 100 mole percent; and
each Q and Q' is independently selected from the group consisting of functionalized and unfunctionalized alkylene of linear, branched, or cyclic structure and combinations thereof, wherein any of the beforementioned groups may be with or without heteroatoms;

each R' is independently selected from the group consisting of hydrogen, methyl, and combinations thereof;
each —X— is independently selected from the group consisting of —O— and —S—; and
each —Z is independently selected from the group consisting of —OH and —SH.

In a separate embodiment for the structure immediately shown above, each Q and Q' can be independently selected from an alkylene group represented by the structure —$(CH_2)_k$—, wherein k is an integer equal to or greater than 1; optionally, one or more hydrogen atom in —$(CH_2)_k$— is independently substituted by one or more halogen atoms, C1-C5 alkyl, amino, hydroxyl or alkoxy groups, or combinations thereof; and optionally, one or more —$CH_2$— in —$(CH_2)_k$— is independently replaced by one or more —O—, —S—, or —$N(R_1)$—. As a non-limiting illustration, each Q and Q' may have the structure: —$CH_2$—$CH_2$—.

The at least one second monomer may be selected from the group consisting of: (meth)acrylamides, (meth)acrylates, allyls, benzoxanes, cinnamyls, epoxies, fumarates, maleates, maleimides, α,β-olefinically unsaturated carboxylic nitriles, oxazolines, oxetanes, styrenes, vinyl esters, vinyl acetates, vinyl amides, vinyl alcohols, vinyl carbonates, vinyl carbamates, vinyl thiocarbamates, vinyl ureas, vinyl ethers, vinyl halides, vinyl imidazoles, vinyl lactams, vinyl pyridines, vinyl silanes, vinyl sulfones, derivatives thereof, and blends thereof. In one particular embodiment, the at least one second monomer is selected from the group consisting of: N-vinyl-2-pyrrolidone, N-vinyl-2-caprolactam, acrylic acid, acrylate salts, methacrylic acid, methacrylate salts, acrylamide, methacrylamide, dimethylaminopropyl methacrylamide, dimethylaminopropyl methacrylate, lauryl methacrylate, dimethylaminopropyl acrylamide, dimethylaminopropyl acrylate, lauryl acrylate, m-isopropenyl-α,α-dimethylbenzyl isocyanate, 2-acrylamido-2-methylpropane sulfonic acid (AMPS), salts of AMPS, derivatives thereof, and blends thereof.

More particularly, the non-homopolymer can be synthesized by polymerizing a first monomer represented by the structure:

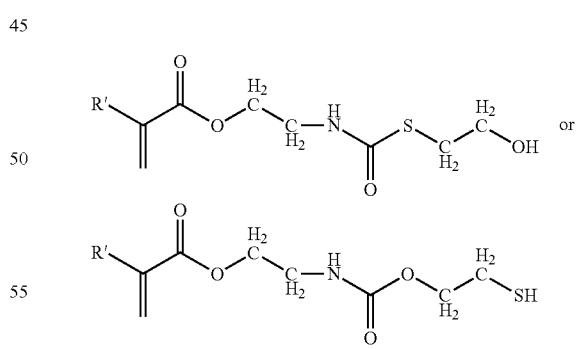

wherein R' is hydrogen or methyl, with at least one second monomer as defined in the immediate above paragraph.

Several non-limiting examples of the invention's non-homopolymers now are presented, with the understanding that the invention fully embraces all such non-homopolymers as set forth above. One non-homopolymer of the invention may be represented by the structure:

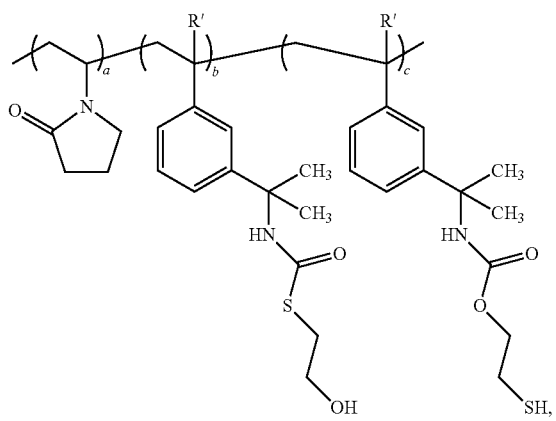

wherein a, b, and c represent molar fractions, and each independently ranges from 0.001 mole percent to 99.999 mole percent, and the sum of a, b, and c is 100 mole percent; and each R is independently selected from the group consisting of hydrogen, methyl, and combinations thereof.

A second non-homopolymer of the invention may be represented by the structure:

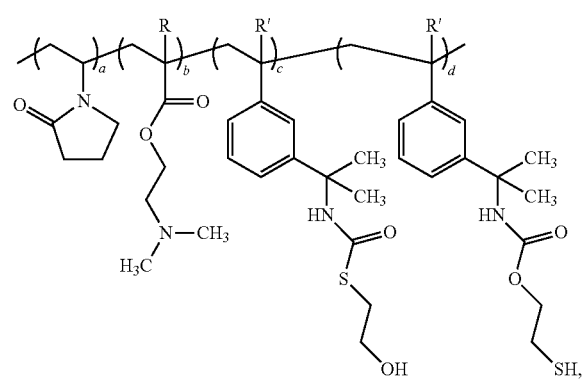

wherein a, b, c, and d represent molar fractions, and each independently ranges from 0.001 mole percent to 99.999 mole percent, and the sum of a, b, c, and d is 100 mole percent; and each R is independently selected from the group consisting of hydrogen, methyl, and combinations thereof.

A third non-homopolymer of the invention may be represented by the structure:

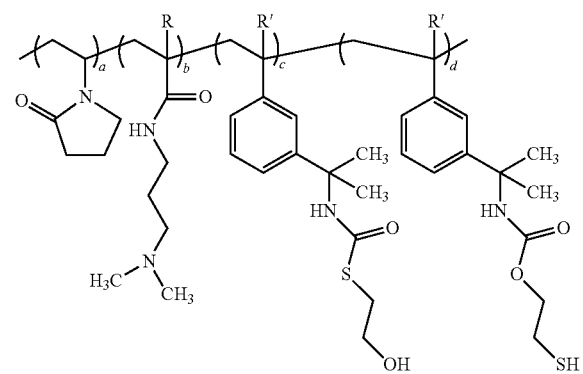

wherein a, b, c, d, and e represent molar fractions, and each independently ranges from 0.001 mole percent to 99.999 mole percent, and the sum of a, b, c, and d is 100 mole percent; and each R is independently selected from the group consisting of hydrogen, methyl, and combinations thereof.

A fourth non-homopolymer of the invention may be represented by the structure:

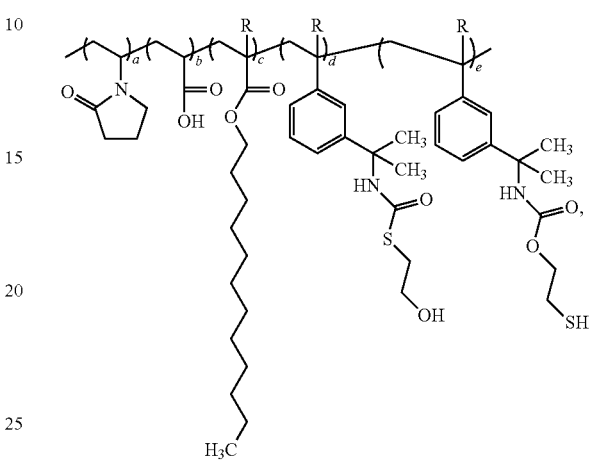

wherein a, b, c, d, and e represent molar fractions, and each independently ranges from 0.001 mole percent to 99.999 mole percent; and each R is independently selected from the group consisting of hydrogen, methyl, and combinations thereof.

A third non-homopolymer of the invention may be represented by the structure:

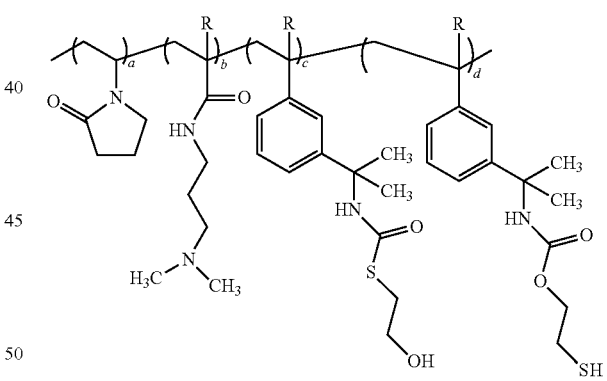

wherein a, b, c, d, and e represent molar fractions, and each independently ranges from 0.001 mole percent to 99.999 mole percent; and each R is independently selected from the group consisting of hydrogen, methyl, and combinations thereof.

The polymers (including homopolymers and non-homopolymers) according to the invention may be readily synthesized by procedures known by those skilled in the art, and include free radical polymerization, emulsion polymerization, ionic chain polymerization, living polymerization, and precipitation polymerization. Free radical polymerization is one such polymerization method, especially when using water-dispersible and/or water-soluble reaction solvent(s), and is described in "Decomposition Rate of Organic Free Radical Polymerization" by K. W. Dixon (section II in *Poly-* mer *Handbook*, volume 1, 4th edition, Wiley-Interscience, 1999), which is hereby incorporated in its entirety by reference.

Compounds capable of initiating the free-radical polymerization include those materials known to function in the prescribed manner, and include the peroxo and azo classes of materials. Exemplary peroxo and azo compounds include, but are not limited to acetyl peroxide; azo bis-(2-amidinopropane)dihydrochloride; azo bis-isobutyronitrile; 2,2'-azo his-(2-methylbutyronitrile); benzoyl peroxide; di-tert-amyl peroxide; di tert-butyl diperphthalate; butyl peroctoate; tert-butyl dicumyl peroxide; tert-butyl hydroperoxide; tert-butyl perbenzoate; tert-butyl permalcate; tert-butyl perisobutylrate; tert-butyl peracetate; tert-butyl perpivalate; para-chlorobenzoyl peroxide; cumene hydroperoxide; diacetyl peroxide; dibenzoyl peroxide; dicumyl peroxide; didecanoyl peroxide; dilauroyl peroxide; diisopropyl peroxodicarbamate; dioctanoyl peroxide; lauroyl peroxide; octanoyl peroxide; succinyl peroxide; and bis-(ortho-toluoyl) peroxide.

Also suitable to initiate the free-radical polymerization are initiator mixtures or redox initiator systems, including; ascorbic acid/iron (II) sulfate/sodium peroxodisulfate, tert-butyl hydroperoxide/sodium disulfite, and tert-butyl hydroperoxide/sodium hydroxymethanesulfinate.

The polymers and compositions comprising the polymers according to the invention can be analyzed by known techniques. The techniques of $^{13}C$ nuclear magnetic resonance (NMR) spectroseopy, gas chromatography (GC), and gel permeation chromatography (GPC) may be useful to decipher polymer identity, residual monomer concentrations, polymer molecular weight, and polymer molecular weight distribution.

Nuclear magnetic resonance (NMR) spectroscopy can be used to probe the polymerization product in terms of chemical properties such as monomeric composition, sequencing and tacticity. Analytical equipment suitable for these analyses includes the Inova 400-MR NMR System by Varian Inc. (Palo Alto, Calif.). References broadly describing NMR include: Yoder, C. H. and Schaeffer Jr., C. D., *Introduction to Multinuclear NMR*, The Benjamin/Cummings Publishing Company, Inc., 1987; and Silverstein, R. M., et al., *Spectrometric identification of Organic Compounds*, John Wiley & Sons, 1981, which are incorporated in their entirety by reference.

Residual monomer levels can be measured by GC, which can be used to indicate the extent of reactant conversion by the polymerization process. GC analytical equipment to perform these tests are commercially available, and include the following units: Series 5880, 5890, and 6890 GC-FID and GC-TCD by Agilent Technologies, Inc. (Santa Clara, Calif.). GC principles are described in *Modern Practice of Gas Chromatography*, third edition (John Wiley & Sons, 1995) by Robert L. Grob and Eugene F. Barry, which is hereby incorporated in its entirety by reference.

GPC is an analytical method that separates molecules based on their hydrodynamic volume (or size) in solution of the mobile phase, such as hydroalcoholic solutions with surfactants. GPC can be employed to determine polymer molecular weight distributions. This technique can be performed on known analytical equipment sold for this purpose, and include the TDAmax™ Elevated Temperature GPC System and the RImax™ Conventional Calibration System by Viscotek™ Corp. (Houston, Tex.). In addition, GPC employs analytical standards as a reference, of which a plurality of narrow-distribution polyethylene glycol and polyethylene oxide standards representing a wide range in molecular weight can be used. These analytical standards are available for purchase from Rohm & Haas Company (Philadelphia, Pa.) and Varian Inc. (Palo Alto, Calif.). GPC is described in the following texts, which are hereby incorporated in their entirety by reference: Schroder, E., et al., *Polymer Characterization*, Hanser Publishers, 1989; Billingham, N.C., *Molar Mass Measurements in Polymer Science*, Halsted Press, 1979; and Billmeyer, F., *Textbook of Polymer Science*, Wiley Interscience, 1984.

In addition to all of the polymerizable compounds, homopolymers, and non-homopolymers that are described above, the invention also provides for compositions comprising them. These compositions may be adhesive, agricultural, biocide, cleaning, coating, encapsulation, membrane, oilfield, performance chemical, or personal care compositions.

Non-limiting examples of compositions comprising the compounds, homopolymers and non-homopolymers according to the invention include performance chemical compositions and personal care compositions.

Polymers of the invention may be used in a wide variety of compositions that serve the human condition, as well as in adhesives, agricultural, biocides, coatings, electronics, household-industrial-institutional (HI&I), inks, membranes, metal fluids, oilfield, paper, paints, plastics, printing, plasters, and wood-care compositions.

Compositions belonging to the personal care/cosmetic and pharmaceutical arts can find utility in altering, delivering an active, enhancing, improving, modifying the appearance, condition, color, health, style of the skin (including face, scalp, and lips), hair, nails, and oral cavity. Many examples and product forms of these compositions are known. These compositions can impart benefits that include, but are not limited to, hair style flexibility, hair style durability, humidity resistance for hair, color and/or color protection, moisturization, wrinkle reduction, protection from ultraviolet radiation, water proofness, water resistance, wear resistance, thermal protection, adhesion, active ingredient delivery, anti-cavity, and/or anti-gingivitis protection. As such, these compositions are sometimes categorized in the following areas: skin care, hair care (both styling and non-styling), sun care, cosmetics (including color cosmetics), antiperspirants, deodorants, oral hygiene, and men's and women's personal hygiene/grooming. In some cases these benefits and care areas overlap with another.

Skin care compositions include those materials used on the body, face, hands, lips, and/or scalp, and are beneficial for many reasons, such as firming, anti-cellulite, moisturizing, nourishing, cleaning, reducing or eliminating the appearance of wrinkles or lentigo, toning, and/or purifying. They also can be used to sanitize.

Today's savvy consumer can identify many of the compositions that serve the sun care area, for example after-fun, children's, beach, self-tan, sports (i.e., being sweatproof, waterproof, resistant to running, or having added UV absorbers and/or antioxidants), sensitive skin products (i.e., having low irritation to the eyes and/or skin, and/or being free of fragrances and/or dyes), daily wear, leave-on hair creams, lotions, styling products, and hair sprays. Typically, sun care products also comprise one or more UV actives, which are those organic and inorganic materials that scatter, absorb, and/or reflect radiation having a wavelength from about 100 nm to about 400 nm. In one aspect, the sun care product protects against UV-A and/or UV-B radiation. UV-A radiation, from about 320 nm to about 400 nm, has the longest wavelength within the UV spectrum, and consequently is the least energetic. While UV-A rays can induce skin tanning, they are liable to induce adverse changes as well, especially in the case of sensitive skin or of skin which is continually exposed to solar radiation. In particular UV-A rays cause a loss of skin elasticity and the appearance of wrinkles, leading to premature skin aging. UV-B rays have shorter wavelengths, from about 290 nm to about 320 nm, and their higher energy can cause erythema and skin burns which may be harmful. Alternatively, sun care products may omit UV actives, and may be regarded as a tanning oil or a tan promoter. Some sun care compositions may promote soothe skin after sun exposure, and/or be formulated for application to the lips, hair, or the area around the eyes. Self-tan compositions, which are products that color skin without requiring full sun exposure, also fit under the sun care umbrella. The many different sun care product formats include may assume a consistency ranging from liquid to semiliquid forms (e.g., milks, creams), to thicker forms like gels, creams, pastes, and even solid- and wax-like forms. Sun care products also may take the form of an aerosol, spray, mist, roll-on, or wipe.

Hair care compositions include shampoos, leave-on and rinse-out conditioners used for conditioning, moisturizing, repairing, hair colors, hair relaxers, and deep conditioners and treatments such as hot oils and waxes, 2-in-1 shampoo/conditioner combination products, 3-in-1 shampoo/conditioner/styling agent. The many types of hair care products can be delivered in an array of formats, including aerosol sprays, pump sprays, gel sprays, mousses, gels, waxes, creams, pomades, spritzes, putties, lacquers, de-frizzing serums, perms, relaxants and colorants.

Color cosmetic compositions include facial make-up, eye makeup, mascaras, lip and nail products. Facial make-up compositions include foundation (liquid, solid, and semi-solid)—skin tinted creams, liquid, sticks, mousses used as a base under make-up, rouge, face powder, blusher, highlighters, face bronzers, concealers, and 2-way cake products.

Personal care/cosmetics also include eye make-up, mascaras, eyeliners, eye shadows, eyebrow pencils and eye pencils. Lip products include lipsticks, lip pencils, lip gloss, transparent bases and tinted lip moisturizers as well as multi-function color sticks that can also be used for cheeks and eyes. Nail products includes nail varnishes/enamels, nail varnish removers, treatments, home-manicure products such as cuticle softeners and nail strengtheners.

In addition to the skin, hair, and sun care compositions summarized above, the polymers related herein also find application in oral care compositions. Non-limiting examples or oral care compositions include toothpastes (including toothpaste gels), denture adhesives, whiteners, anesthetics, and dental floss and related products. These oral care compositions may assist in the whitening of teeth and/or the delivery of active agents, such as (but not limited to) anti-bacterial agents, anti-gingivitis agents, and favor agents, to the oral cavity. These compositions may take any product format, such as pastes, gels, creams, solutions, dispersions, rinses, flosses, aerosols, powders, and lozenges.

Men's and women's grooming products includes shaving products and toiletries, which may find use in preparing the skin and/or hair for dry or wet shaving. In addition, these compositions may help to moisturize, cool, and/or soothe skin. A variety of product forms are known, a few of which are foams, gels, creams, sticks, oils, solutions, tonics, balms, aerosols, mists, sprays, and wipes.

The polymer can also be used in other personal care/cosmetic applications, such as an absorbent material in appropriate applications such as diapers, incontinence products, feminine products, and other related products.

The polymers described herein also find application in bath and shower compositions, such as foams, gels, salts, oils, balls, liquids, powders and pearls. Also included are bar soaps, body washes, shower gels, cleansers, gels, oils, foams, scrubs and creams. As a natural extension of this category, these compositions also include liquid soaps and hand sanitizers used for cleaning hands.

The polymer of the invention can be used in combination with one or more additional personal care/cosmetically acceptable additives chosen from, for example, conditioning agents, protecting agents, such as, for example, hydrosoluble, liposoluble and water-insoluble UV filters, antiradical agents, antioxidants, vitamins and pro-vitamins, fixing agents, oxidizing agents, reducing agents, dyes, cleansing agents, anionic, cationic, nonionic and amphoteric surfactants, thickeners, perfumes, pearlizing agents, stabilizers, pH adjusters, filters, preservatives, hydroxy acids, various cationic, anionic and nonionic polymers, cationic and nonionic polyether associative polyurethanes, vegetable oils, mineral oils, synthetic oils, polyols such as glycols and glycerol, silicones, aliphatic alcohols, colorants, bleaching agents, highlighting agents and sequestrants.

For some embodiments, it may be preferred to add one or more preservatives and/or antimicrobial agents, such as, but not limited to, benzoic acid, sorbic acid, dehydroacetic acid, piroctone olamine, DMDM hydantoin, IPBC, triclosan, bronopol, formaldehyde, isothiazolinones, nitrates/nitrites, parabens, phenoxyethanol, potassium sorbate, sodium benzoate, sulphites, and sulphur dioxide. Combinations of preservatives may be used.

In other embodiments it may be desirable to incorporate preservative boosters/solvents, select examples of which include caprylyl glycol, hexylene glycol, pentylene glycol, ethylhexylglycerin, caprylhydroxamic acid, and glyceryl caprylate.

Humectants, which include glycerin, butylene glycol, propylene glycol, sorbitol, mannitol, and xylitol may be added.

Polysaccharides, such as gum Arabic, may be included as well.

It may be desirable to include one or more ingredients described in the prior art disclosure IPCOM000186541D, IPCOM000128968D, and IPCOM000109682D on www.ip.com, the contents of this disclosure are incorporated herein their entirety by reference.

Further reference to formulary co-ingredients and product forms include the disclosures in U.S. 2010/0183532, paragraphs [0096]-[0162] and WO 2010/105050, paragraphs [0053]-[0069], the contents of which are hereby incorporated by reference.

These additives may be present in the composition according to the invention in proportions that may range from about 0% to about 20% by weight in relation to the total weight of the composition. The precise amount of each additive may be easily determined by an expert in the field according to its nature and its function.

Examples of these co-ingredients and many others can be found in the following references, each of which is herein incorporated in its entirety by reference: "Inventory and common nomenclature of ingredients employed in cosmetic products," *Official Journal of the European Union*, May, 4, 2006, pages L 97/1 through L 97/528; and *International Cosmetic Ingredient Dictionary and Handbook*, 13$^{th}$ edition, ISBN: 1882621476, published by The Personal Care Products Council in January 2010.

Any known conditioning agent is useful in the personal care/cosmetic compositions of this invention. Conditioning agents function to improve the cosmetic properties of the hair, particularly softness, thickening, untangling, feel, and static electricity and may be in liquid, semi-solid, or solid form such as oils, waxes, or gums. Similarly, any known skin-altering agent is useful in the compositions of this invention. A few examples of conditioning agents include cationic polymers, cationic surfactants and cationic silicones. Conditioning agents may be chosen from synthesis oils, mineral oils, vegetable oils, fluorinated or perfluorinated oils, natural or synthetic waxes, silicones, cationic polymers, proteins and hydrolyzed proteins, ceramide type compounds, cationic surfactants, fatty amines, fatty acids and their derivatives, as well as mixtures of these different compounds.

The synthesis oils include polyolefins, e.g., poly-α-olefins such as polybutenes, polyisobutenes and polydecenes. The polyolefins can be hydrogenated. The mineral oils suitable for use in the compositions of the invention include hexadecane and oil of paraffin. Suitable animal and vegetable oils include sunflower, corn, soy, avocado, jojoba, squash, raisin seed, sesame seed, walnut oils, fish oils, glycerol tricaprocaprylate, Purcellin oil or liquid jojoba. Suitable natural or synthetic oils include eucalyptus, lavender, vetiver, litsea cubeba, lemon, sandalwood, rosemary, chamomile, savory, nutmeg, cinnamon, hyssop, caraway, orange, geranium, cade, and bergamot. Suitable natural and synthetic waxes include carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax.

The cationic polymers that may be used as a conditioning agent according to the invention are those known to improve the cosmetic properties of hair treated by detergent compositions. The expression "cationic polymer" as used herein, indicates any polymer containing cationic groups and/or ionizable groups in cationic groups. The cationic polymers used generally have a molecular weight the average number of which falls between about 500 and 5,000,000, for example between 1000 and 3,000,000. Cationic polymers may be chosen from among those containing units including primary, secondary, tertiary, and/or quaternary amine groups that may either form part of the main polymer chain or a side chain. Useful cationic polymers include known polyamine, polyaminoamide, and quaternary polyammonium types of polymers, such as:

(1) homopolymers and copolymers derived from acrylic or methacrylic esters or amides. The copolymers can contain one or more units derived from acrylamides, methacrylamides, diacetone acrylamides, acrylamides and methacrylamides, acrylic or methacrylic acids or their esters, vinyllactams such as vinyl pyrrolidone or vinyl caprolactam, and vinyl esters. Specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name Gafquat® by International Specialty Products; the dimethyl amino ethyl methacrylate/vinyl caprolactam/vinyl pyrrolidone terpolymers, such as the product sold under the name Gaffix® VC 713 by International Specialty Products; the vinyl pyrrolidone/methacrylamidopropyl dimethylamine copolymer, marketed under the name Styleze® CC-10 by International Specialty Products; the vinyl pyrrolidone/quaternized dimethyl amino propyl methacrylamide copolymers such as the product sold under the name Gafquat® HS-100 by International Specialty Products; and the vinyl pyrrolidone/ dimethylaminopropyl methacrylamide/$C_9$-$C_{24}$ alkyldimethylaminopropyl methacrylic acid quaternized terpolymers described in U.S. Pat. No. 6,207,778 and marketed under the name Styleze®W-20 by International Specialty Products.

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as the hydroxy alkyl cellulose, and the hydroxymethyl-, hydroxyethyl- or hydroxypropylcellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalkylene polyamines with polycarboxylic acids followed by alkylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347.

(9) the cyclopolymers of alkyl dialyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride. Polymers of this type are described particularly in U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020.

(11) quaternary polyammonium polymers, including, for example, Mirapol® A 15, Mirapol® AD1, Mirapol® AZ1, and Mirapol® 175 products sold by Miranol.

(12) the quaternary polymers of vinyl pyrrolidone and vinyl imidazole such as the products sold under the names Luviquat® FC 905, FC 550, and FC 370 by BASF.

(13) quaternary polyamines.

(14) reticulated polymers known in the art.

Other cationic polymers that may be used within the context of the invention are cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin. In one aspect, the cationic polymers may be derivatives of quaternary cellulose ethers, the homopolymers and copolymers of dimethyl diallyl ammonium chloride, quaternary polymers of vinyl pyrrolidone and vinyl imidazole, and mixtures thereof.

The conditioning agent can be any silicone known by those skilled in the art to be useful as a conditioning agent. The silicones suitable for use according to the invention include polyorganosiloxanes that are insoluble in the composition. The silicones may be present in the form of oils, waxes, polymers, or gums. They may be volatile or non-volatile. The silicones can be selected from polyalkyl siloxanes, polyaryl siloxanes, polyalkyl aryl siloxanes, silicone gums and polymers, and polyorgano siloxanes modified by organofunctional groups, and mixtures thereof. Suitable polyalkyl siloxanes include polydimethyl siloxanes with terminal trimethyl silyl groups or terminal dimethyl silanol groups (dimethiconol) and polyalkyl ($C_1$-$C_{20}$) siloxanes. Suitable polyalkyl aryl siloxanes include polydimethyl methyl phenyl siloxanes and polydimethyl diphenyl siloxanes, linear or branched. The silicone gums suitable for use herein include polydiorganosiloxanes including those having a number-average molecular weight between 200,000 and 1,000,000, used alone or mixed with a solvent. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane. Suitable silicone polymers include silicones with a dimethyl/trimethyl siloxane structure and polymers of the trimethyl siloxysilicate type. The organomodified silicones suitable for use in the invention include silicones such as those previously defined and containing one or more organofunctional groups attached by means of a hydrocarbon radical and grafted siliconated polymers. In one embodiment the silicones are amino functional silicones. The silicones may be used in the form of emulsions, nano-emulsions, or micro-emulsions.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one $C_1$-$C_{18}$ alkyl. Hydrolyzed proteins include Croquat™ L, in which the quaternary ammonium groups include a $C_{12}$ alkyl group, Croquat™ M, in which the quaternary ammonium groups include $C_{10}$-$C_{18}$ alkyl groups, Croquat™ S in which the quaternary ammonium groups include a $C_{18}$ alkyl group and Crotein Q in which the quaternary ammonium groups include at least one $C_1$-$C_{18}$ alkyl group. These products are sold by Croda. The conditioning agent can comprise quaternized vegetable proteins such as wheat, corn, or soy proteins such as cocodimonium hydrolyzed wheat protein, laurdimonium hydrolyzed wheat protein and steardimonium hydrolyzed wheat protein.

The conditioning agent can be a ceramide type of compound such as a ceramide, a glycoceramide, a pseudoceramide, or a neoceramide. These compounds can be natural or synthetic. Compounds of the ceramide type are, for example, described in Patents pending DE4424530, DE4424533, DE4402929, DE4420736, WO95/23807, WO94/07844, EP-A-0646572, WO95/16665, FR-2 673 179, EP-A-0227994, WO 94/07844, WO 94/24097, and WO 94/10131. Ceramide type compounds useful herein include 2-N-linoleoyl amino-octadecane-1,3-diol, 2-N-oleoyl amino-octadecane-1,3-diol, 2-N-palmitoyl amino-octadecane-1,3-diol, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl) malonamide, N(2-hydroxy ethyl)-N-(3-cetoxyl-2-hydroxy propyl) amide of cetylic acid, N-docosanoyl N-methyl-D-glucamine and mixtures of such compounds.

The conditioning agent can be a cationic surfactant such as a salt of a primary, secondary, or tertiary fatty amine, optionally polyoxyalkylenated, a quaternary ammonium salt, a derivative of imadazoline, or an amine oxide. Suitable examples include mono-, di-, or tri-alkyl quaternary ammonium compounds with a counter-ion such as a chloride, methosulfate, tosylate, etc. including, but not limited to, cetrimonium chloride, dicetyldimonium chloride, behentrimonium methosulfate, and the like. The presence of a quaternary ammonium compound in conjunction with the polymer described above reduces static and enhances combing of hair in the dry state. The polymer also enhances the deposition of the quaternary ammonium compound onto the hair substrate thus enhancing the conditioning effect of hair.

The conditioning agent can be any fatty amine known to be useful as a conditioning agent; e.g. dodecyl, cetyl or stearyl amines, such as stearamidopropyl dimethylamine. The conditioning agent can be a fatty acid or derivatives thereof known to be useful as conditioning agents. Suitable fatty acids include myristic acid, palmitic acid, stearic acid, behenic acid, oleic acid, linoleic acid, and isostearic acid. The derivatives of fatty acids include carboxylic ester acids including mono-, di-, tri- and tetra-carboxylic acids.

The conditioning agent can be a fluorinated or perfluorinated oil. Fluorinated oils include perfluoropolyethers described in EP-A-486135 and the fluorohydrocarbon compounds described in WO 93/11103. The fluoridated oils may also be fluorocarbons such as fluoramines, e.g., perfluorotributylamine, fluoridated hydrocarbons, such as perfluorodecahydronaphthalene, fluoroesters, and fluoroethers. Of course, mixtures of two or more conditioning agents can be used.

The conditioning agent or agents can be present in an amount from about 0.001% to about 20%, particularly from about 0.01% to about 10%, and even more particularly from about 0.1% to about 3% by weight based on the total weight of the final composition. The personal care/cosmetic compositions of the invention can contain one or more protecting agents in combination with the above-described polymer to prevent or limit the degrading effects of natural physical and/or chemical assaults on the keratinous materials.

The protecting agent can be chosen from hydrosoluble, liposoluble and water-insoluble UV filters, antiradical agents, antioxidants, vitamins and pro-vitamins. The above-described cationic polymer enhances the deposition of these materials onto the hair or skin substrate enhancing protection of hair to UV damage. Organic UV filters (systems that filter out UV rays) can be chosen from among hydrosoluble or liposoluble filters, whether siliconated or nonsiliconated, and mineral oxide particles, the surface of which may be treated. Hydrosoluble organic UV filters may be chosen from para-amino benzoic acid and its salts, anthranilic acid and its salts, salicylic acid and its salts, hydroxy cinnamic acid and its salts, sulfonic derivatives of benzothiazoles, benzimidizoles, benzoxazoles and their salts, sulfonic derivatives of benzophenone and their salts, sulfonic derivatives of benzylidene camphor and their salts, derivatives of benzylidene camphor substituted by a quaternary amine and their salts, derivatives of phthalydene-camphosulfonic acids and their salts, sulfonic derivatives of benzotriazole, and mixtures thereof. Hydrophilic polymers, which have light-protective qualities against UV rays, can be used. These include polymers containing benzylidene camphor and/or benzotriazole groups.

Suitable liposoluble organic UV filters include derivatives of para-aminobenzoic acid, such as the esters or amides of para-aminobenzoic acid; derivatives of salicylic acid; derivatives of benzophenone; derivatives of dibenzoyl methane; derivatives of diphenyl acrylates; derivatives of benzofurans; UV filter polymers containing one or more silico-organic residues; esters of cinnamic acid; derivatives of camphor; derivatives of trianilino-s-triazine; the ethylic ester urocanic acid; benzotriazoles; derivatives of hydroxy phenyl triazine; bis-resorcinol-dialkyl amino triazine; and mixtures thereof. The liposoluble (or lipophilic) organic UV filter can be chosen from octyl salicylate; 4-tert-butyl-4'-methoxy dibenzoyl methane; octocrylene; 4-methoxy cinnamate; 2-ethylhexyl [2-ethylhexyl 4-methoxycinnamate]; and 2-(2H-benzotriazol-2-yl)-4-methyl-6-[2-methyl-3-[1,3,3,3-tetramethyl-1-[(trimethyl silyl)oxy]disiloxanyl]propynyl]phenol. Other UV filters that may be useful are derivatives of benzophenones such as 2-hydroxy-4-methoxy benzophenone-5-sulfonic acid, 2-hydroxy-4-methoxy benzophenone, derivatives of benzalmalonates such as poly dimethyl/methyl (3(4-(2,2-bis-ethoxy carbonyl vinyl)-phenoxy)-propenyl)siloxane, derivatives of benzylidene camphor such as b-b'camphosulfonic [1-4 divinylbenzene]acid and derivatives of benzimidazole such as 2-phenyl-benzimidazol-5-sulfonic acid. Water-insoluble UV filters include various mineral oxides. The mineral oxides may be selected from among titanium oxides, zinc oxides, and cerium oxides. The mineral oxides can be used in the form of ultrafine nanoparticles. For example, the UV filters can include Escalol® HP-610 (dimethylpabamido propyl laurdimonium tosylate and propylene glycol stearate) or Crodasorb HP (polyquaternium 59).

The antioxidants or antiradical agents can be selected from phenols such as BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, and lactoferrin.

The vitamins can be selected from ascorbic acid (vitamin C), vitamin E, vitamin E acetate, vitamin E phosphate, B vitamins such as B3 and B5, vitamin PP, vitamin A, and derivatives thereof. The provitamins can be selected from panthenol and retinol.

The protecting agent can be present in an amount from about 0.001% to about 20% by weight, particularly from about 0.01% to about 10% by weight, and more particularly from 0.1% to about 5% by weight of the total weight of the final composition.

The composition of the invention can contain a fixing agent in combination with the above-described polymer. The fixing agent can be an anionic polymer chosen from polymers containing carboxylic units derived from unsaturated carboxylic mono- or polyacids of the formula:

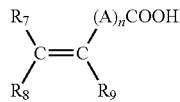

in which n is a whole number from 0 to 10, A denotes a methylene group, optionally bonded to the carbon atom of the unsaturated group or to a neighboring methylene group when n is greater than 1 by means of a heteroatom like oxygen or sulfur, $R_7$ denotes a hydrogen atom, a phenyl or benzyl group, $R_8$ denotes a hydrogen atom, a lower alkyl or carboxyl group, $R_9$ denotes a hydrogen atom, a lower alkyl group, a —$CH_2$—COOH, phenyl or benzyl group and polymers containing units derived from sulfonic acid like vinylsulfonic, styrenesulfonic, acrylamidoalkylsulfonic units.

The fixing agent can be an amphoteric polymer chosen from the polymer containing recurring units derived from:
a) at least one monomer chosen from acrylamides or methacrylamides substituted on the nitrogen with an alkyl radical,
b) at least one acid copolymer containing one or more reactive carboxyl groups, and
c) at least one basic comonomer, such as esters with primary, secondary, tertiary, and quaternary amino substituents of acrylic and methacrylic acids and the product of quaternization of dimethylaminoethyl methacrylate with dimethyl or diethyl sulfate.

The fixing agent can be a nonionic polymer chosen from polyalkyloxazolines; vinyl acetate homopolymers; vinyl acetate and acrylic ester copolymers; vinyl acetate and ethylene copolymers; vinyl acetate and maleic ester copolymers; polyethylene and maleic anhydride copolymers; homopolymers of alkyl acrylates; homopolymers of alkyl methacrylates; copolymers of acrylic esters; copolymers of alkyl acrylates and alkyl methacrylates; copolymers of acrylonitrile and a nonionic monomer chosen from among butadiene and alkyl (meth)acrylates; copolymers of alkyl acrylate and urethane; and polyamides. The fixing agent can be a functionalized or unfunctionalized, silicone or non-silicone polyurethane. The fixing polymer can be a polymer of the grafted silicone type containing a polysiloxane portion and a portion consisting of a nonsilicone organic chain, with one of the two portions forming the main chain of the polymer, and with the other being grafted onto said main chain.

The fixing agent can be present in the composition in a relative weight concentration between about 0.1% to about 10%, for example, from about 0.5% to about 5%.

The personal care/cosmetic composition of the invention can contain an oxidizing agent in combination with the above-described polymer. The oxidizing agent can be chosen from the group of hydrogen peroxide, urea peroxide, alkali metal bromates, ferricyanides, persalts, and redox enzymes, optionally with their respective donor or cofactor. For example, the oxidizing agent can be hydrogen peroxide. The oxidizing agent can be a solution of oxygenated water whose titer varies from 1 to 40 volumes.

The personal care/cosmetic composition of the invention can contain at least one reducing agent in combination with the above-described polymer in amounts from about 0.01% to about 30%, particularly from about 0.05% to about 20% of the total weight of the composition. The reducing agents can be selected from thiols, like cysteine, thioglycolic acid, thiolactic acid, their salts and esters, cysteamine, and its salts or sulfites. In the case of compositions intended for bleaching, ascorbic acid, its salts and its esters, erythorbic acid, its salts and its esters, and sulfinates, like sodium hydroxymethanesulfinate can be used.

The personal care/cosmetic composition of the invention can contain a dye in combination with the above-described polymer. The dye can be selected from the group consisting of neutral acid or cationic nitrobenzene dyes, neutral acid or cationic azo dyes, quinone dyes, neutral, acid or cationic anthraquinone dyes, azine dyes, triarylmethane dyes, indoamine dyes and natural dyes. The dye or dyes can be present in a concentration from about 0.001% to about 20%, and particularly from about 0.005% to about 10% based on the total weight of the composition.

The personal care/cosmetic composition of the invention can contain at least one amphoteric polymer or a cationic polymer in combination with the above-described polymer. Suitable cationic polymers include a poly(quaternary ammonium) consisting of recurrent units corresponding to the following formulas:

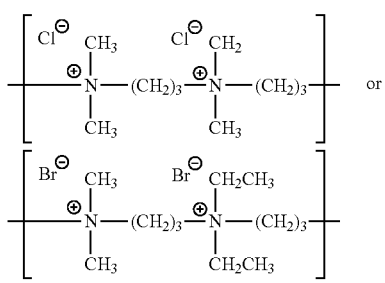

Suitable amphoteric polymers include a copolymer containing at least one acrylic acid and a dimethyldiallyammonium salt as a monomer. The cationic or amphoteric polymer or polymers can be present in an amount from about 0.01% to about 10%, particularly from about 0.05% to about 5%, and more particularly from about 0.1% to about 3% by weight of the total weight of the composition.

In addition, the personal care/cosmetic compositions can include at least one surfactant in combination with the above-described polymer. The surfactant can be present in an amount from about 0.1% to about 60%, particularly from about 1% to about 40%, and more particularly from about 5% to about 30% by weight based on the total weight of the composition. The surfactant may be chosen from among anionic, amphoteric, or non-ionic surfactants, or mixtures of them known to be useful in personal care/cosmetic compositions.

One or more suitable thickeners or viscosity increasing agents may be included in combination with the above-described polymer in the personal care/cosmetic compositions of the invention. Suitable thickeners and/or viscosity increasing agents include: acetamide MEA, acrylamide/ethalkonium chloride acrylate copolymer, acrylamide/ethyltrimonium chloride acrylate/ethalkonium chloride acrylate copolymer, acrylamides copolymer, acrylamide/sodium acrylate copolymer, acrylamide/sodium acryloyldimethyltaurate copolymer, acrylates/acetoacetoxyethyl methacrylate copolymer, acrylates/beheneth-25 methacrylate copolymer, acrylates/C10-C30 alkyl acrylate crosspolymer, acrylates/ceteth-20 itaconate copolymer, acrylates/ceteth-20 methacrylate copolymer, acrylates/laureth-25 methacrylate copolymer, acrylates/palmeth-25 acrylate copolymer, acrylates/palmeth-25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylic acid/acrylonitrogens copolymer, adipic acid/methyl DEA crosspolymer, agar, agarose, *alcaligenes* polysaccharides, algin, alginic acid, almondamide DEA, almondamidopropyl betaine, aluminum/magnesium hydroxide stearate, ammonium acrylates/acrylonitrogens copolymer, ammonium acrylates copolymer, ammonium acryloyldimethyltaurate/vinyl formamide copolymer, ammonium acryloyldimethyltaurate/vp copolymer, ammonium alginate, ammonium chloride, ammonium polyacryloyldimethyl taurate, ammonium sulfate, amylopectin, apricotamide DEA, apricotamidopropyl betaine, arachidyl alcohol, arachidyl glycol, *arachis hypogaea* (peanut) flour, ascorbyl methylsilanol pectinate, *astragalus gummifer* gum, attapulgite, *avena sativa* (oat) kernel flour, avocadamide DEA, avocadamidopropyl betaine, azelamide MEA, babassuamide DEA, babassuamide MEA, babassuamidopropyl betaine, behenamide DEA, behenamide MEA, behenamidopropyl betaine, behenyl betaine, bentonite, butoxy chitosan, *caesalpinia spinosa* gum, calcium alginate, calcium carboxymethyl cellulose, calcium carrageenan, calcium chloride, calcium potassium carbomer, calcium starch octenylsuccinate, C20-C40 alkyl stearate, canolamidopropyl betaine, capramide DEA, capryl/capramidopropyl betaine, carbomer, carboxybutyl chitosan, carboxymethyl cellulose acetate butyrate, carboxymethyl chitin, carboxymethyl chitosan, carboxymethyl dextran, carboxymethyl hydroxyethylcellulose, carboxymethyl hydroxypropyl guar, carnitine, cellulose acetate propionate carboxylate, cellulose gum, *ceratonia siliqua* gum, cetearyl alcohol, cetyl alcohol, cetyl babassuate, cetyl betaine, cetyl glycol, cetyl hydroxyethylcellulose, chimyl alcohol, cholesterol/hdi/pullulan copolymer, cholesteryl hexyl dicarbamate pullulan, citrus *aurantium dulcis* (orange) peel extract, cocamide DEA, cocamide MEA, cocamide mipa, cocamidoethyl betaine, cocamidopropyl betaine, cocamidopropyl hydroxysultaine, coco-betaine, coco-hydroxysultaine, coconut alcohol, coco/oleamidopropyl betaine, coco-sultaine, cocoyl sarcosinamide DEA, cornamide/cocamide DEA, cornamide DEA, croscarmellose, crosslinked *bacillus*/glucose/sodium glutamate ferment, *cyamopsis tetragonoloba* (guar) gum, decyl alcohol, decyl betaine, dehydroxanthan gum, dextrin, dibenzylidene sorbitol, diethanolaminooleamide DEA, diglycol/chdm/isophthalates/sip copolymer, dihydroabietyl behenate, dihydrogenated tallow benzylmonium hectorite, dihydroxyaluminum aminoacetate, dimethicone/PEG-10 crosspolymer, dimethicone/PEG-15 crosspolymer, dimethicone propyl pg-betaine, dimethylacrylamide/acrylic acid/polystyrene ethyl methacrylate copolymer, dimethylacrylamide/sodium acryloyldimethyltaurate crosspolymer, disteareth-100 IPDI, dmapa acrylates/acrylic acid/acrylonitrogens copolymer, erucamidopropyl hydroxysultaine, ethylene/sodium acrylate copolymer, gelatin, gellan gum, glyceryl alginate, glycine soja (soybean) flour, guar hydroxypropyltrimonium chloride, hectorite, hyaluronic acid, hydrated silica, hydrogenated potato starch, hydrogenated tallow, hydrogenated tallowamide DEA, hydrogenated tallow betaine, hydroxybutyl methylcellulose, hydroxyethyl acrylate/sodium acryloyldimethyl taurate copolymer, hydroxyethylcellulose, hydroxyethyl chitosan, hydroxyethyl ethylcellulose, hydroxyethyl stearamide-mipa, hydroxylauryl/hydroxymyristyl betaine, hydroxypropylcellulose, hydroxypropyl chitosan, hydroxypropyl ethylenediamine carbomer, hydroxypropyl guar, hydroxypropyl methylcellulose, hydroxypropyl methylcellulose stearoxy ether, hydroxypropyl starch, hydroxypropyl starch phosphate, hydroxypropyl xanthan gum, hydroxystearamide MEA, isobutylene/sodium maleate copolymer, isostearamide DEA, isostearamide MEA, isostearamide mipa, isostearamidopropyl betaine, lactamide MEA, lanolinamide DEA, lauramide DEA, lauramide MEA, lauramide mipa, lauramide/myristamide DEA, lauramidopropyl betaine, lauramidopropyl hydroxysultaine, laurimino bispropanediol, lauryl alcohol, lauryl betaine, lauryl hydroxysultaine, lauryl/myristyl glycol hydroxypropyl ether, lauryl sultaine, lecithinamide DEA, linoleamide DEA, linoleamide MEA, linoleamide mipa, lithium magnesium silicate, lithium magnesium sodium silicate, *macrocystis pyrifera* (kelp), magnesium alginate, magnesium/aluminum/hydroxide/carbonate, magnesium aluminum silicate, magnesium silicate, magnesium trisilicate, methoxy PEG-22/dodecyl glycol copolymer, methylcellulose, methyl ethylcellulose, methyl hydroxyethylcellulose, microcrystalline cellulose, milkamidopropyl betaine, minkamide DEA, minkamidopropyl betaine, mipa-myristate, montmorillonite, moroccan lava clay, myristamide DEA, myristamide MEA, myristamide mipa, myristamidopropyl betaine, myristamidopropyl hydroxysultaine, myristyl alcohol, myristyl betaine, natto gum, nonoxynyl hydroxyethylcellulose, oatamide MEA, oatamidopropyl betaine, octacosanyl glycol isostearate, octadecene/MA copolymer, oleamide DEA, oleamide MEA, oleamide mipa, oleamidopropyl betaine, oleamidopropyl hydroxysultaine, oleyl betaine, olivamide DEA, olivamidopropyl betaine, oliveamide MEA, palmamide DEA, palmamide MEA, palmamide mipa, palmamidopropyl betaine, palmitamide DEA, palmitamide MEA, palmitamidopropyl betaine, palm kernel alcohol, palm kernelamide DEA, palm kernelamide MEA, palm kernelamide mipa, palm kernelamidopropyl betaine, peanutamide MEA, peanutamide mipa, pectin, PEG-800, PEG-crosspolymer, PEG-150/decyl alcohol/smdi copolymer, PEG-175 diisostearate, PEG-190 distearate, PEG-15 glyceryl tristearate, PEG-140 glyceryl tristearate, PEG-240/hdi copolymer bis-decyltetradeceth-20 ether, PEG-100/ipdi copolymer, PEG-180/laureth-50/tmmg copolymer, PEG-10/lauryl dimethicone crosspolymer, PEG-15/lauryl dimethicone crosspolymer, PEG-2,000, PEG-5,000, PEG-7,000, PEG-9,000, PEG-14,000, PEG-20,000, PEG-23,000, PEG-25,000, PEG-45,000, PEG-65,000, PEG-90,000, PEG-115,000, PEG-160,000, PEG-180,000, PEG-120 methyl glucose trioleate, PEG-180/octoxynol-40/tmmg copolymer, PEG-150 pentaerythrityl tetrastearate, PEG-4 rapeseedamide, PEG-150/stearyl alcohol/smdi copolymer, *phaseolus angularis* seed powder, *polianthes tuberosa* extract, polyacrylate-3, polyacrylic acid, polycyclopentadiene, polyether-1, polyethylene/isopropyl maleate/ma copolyol, polyglyceryl-3 disiloxane dimethicone, polyglyceryl-3 polydimethylsiloxyethyl dimethicone, polymethacrylic acid, polyquaternium-52, polyvinyl alcohol, potassium alginate, potassium aluminum polyacrylate, potassium carbomer, potassium carrageenan, potassium chloride, potassium palmate, potassium polyacrylate, potassium sulfate, potato starch modified, PPG-2 cocamide, PPG-1 hydroxyethyl caprylamide, PPG-2 hydroxyethyl cocamide, PPG-2 hydroxyethyl coco/isostearamide, PPG-3 hydroxyethyl soyamide, PPG-14 laureth-60 hexyl dicarbamate, PPG-14 laureth-60 isophoryl dicarbamate, PPG-14 palmeth-60 hexyl dicarbamate, propylene glycol alginate, PVP/decene copolymer, PVP montmorillonite, *pyrus cyclonia* seed, *pyrus malus* (apple) fiber, rhizobian gum, ricebranamide DEA, ricinoleamide DEA, ricinoleamide MEA, ricinoleamide mipa, ricinoleamidopropyl betaine, ricinoleic acid/adipic acid/aeea copolymer, *rosa multiflora* flower wax, sclerotium gum, sesamide DEA, sesamidopropyl betaine, sodium acrylate/acryloyldimethyl taurate copolymer, sodium acrylates/acrolein copolymer, sodium acrylates/acrylonitrogens copolymer, sodium acrylates copolymer, sodium acrylates crosspolymer, sodium acrylate/sodium acrylamidomethylpropane sulfonate copolymer, sodium acrylates/vinyl isodecanoate crosspolymer, sodium acrylate/vinyl alcohol copolymer, sodium carbomer, sodium carboxymethyl chitin, sodium carboxymethyl dextran, sodium carboxymethyl beta-glucan, sodium carboxymethyl starch, sodium carrageenan, sodium cellulose sulfate, sodium chloride, sodium cyclodextrin sulfate, sodium hydroxypropyl starch phosphate, sodium isooctylene/ma copolymer, sodium magnesium fluorosilicate, sodium oleate, sodium palmitate, sodium palm kernelate, sodium polyacrylate, sodium polyacrylate starch, sodium polyacryloyldimethyl taurate, sodium polygammaglutamate, sodium polymethacrylate, sodium polystyrene sulfonate, sodium silicoaluminate, sodium starch octenylsuccinate, sodium stearate, sodium stearoxy PG-hydroxyethylcellulose sulfonate, sodium styrene/acrylates copolymer, sodium sulfate, sodium tallowate, sodium tauride acrylates/acrylic acid/acrylonitrogens copolymer, sodium tocopheryl phosphate, *solanum tuberosum* (potato) starch, soyamide DEA, soyamidopropyl betaine, starch/acrylates/acrylamide copolymer, starch hydroxypropyltrimonium chloride, stearamide amp, stearamide DEA, stearamide DEA-distearate, stearamide diba-stearate, stearamide MEA, stearamide MEA-stearate, stearamide mipa, stearamidopropyl betaine, steareth-60 cetyl ether, steareth-100/PEG-136/hdi copolymer, stearyl alcohol, stearyl betaine, *sterculia urens* gum, synthetic fluorphlogopite, tallamide DEA, tallow alcohol, tallowamide DEA, tallowamide MEA, tallowamidopropyl betaine, tallowamidopropyl hydroxysultaine, tallowamine oxide, tallow betaine, tallow dihydroxyethyl betaine, *tamarindus indica* seed gum, tapioca starch, tea-alginate, tea-carbomer, tea-hydrochloride, trideceth-2 carboxamide MEA, tridecyl alcohol, triethylene glycol dibenzoate, trimethyl pentanol hydroxyethyl ether, *triticum vulgare* (wheat) germ powder, *triticum vulgare* (wheat) kernel flour, *triticum vulgare* (wheat) starch, tromethamine acrylates/acrylonitrogens copolymer, tromethamine magnesium aluminum silicate, undecyl alcohol, undecylenamide DEA, undecylenamide MEA, undecylenamidopropyl betaine, welan gum, wheat germamide DEA, wheat germamidopropyl betaine, xanthan gum, yeast beta-glucan, yeast polysaccharides and *zea mays* (corn) starch.

In one such embodiment, the thickeners or viscosity increasing agents include carbomers, Aculyn™ and Stabileze®, e.g., crosslinked acrylic acid, crosslinked poly(methylvinyl ether/maleic anhydride) copolymer, acrylamides, carboxymethyl cellulose, and the like.

The personal care/cosmetic compositions may be used to wash and treat keratinous material such as hair, skin, eyelashes, eyebrows, fingernails, lips, and hairy skin.

The personal care/cosmetic compositions can be detergent compositions such as shampoos, bath gels, and bubble baths. In this mode, the compositions will comprise a generally aqueous washing base. The surfactant or surfactants that form the washing base may be chosen alone or in blends, from known anionic, amphoteric, or non-ionic surfactants. The quantity and quality of the washing base must be sufficient to impart a satisfactory foaming and/or detergent value to the final composition. The washing base can be from about 4% to about 50% by weight, particularly from about 6% to about 35% by weight, and even more particularly from about 8% to about 25% by weight of the total weight of the final composition.

The pH of the composition applied to the keratinous material is generally between 2 and 12. In one embodiment, the pH is from about 3 to about 8, and may be adjusted to the desired value by means of acidifying or alkalinizing agents that are well-known in the state of the art. Thus, the composition of the invention can contain at least one alkalizing or acidifying agent in amounts from about 0.01% to about 30% based on the total weight of the composition.

The alkalizing agent can be chosen from ammonia, alkali carbonates, alkanolamines, like mono-, di- and triethanolamines, as well as their derivatives, hydroxyalkylamines and ethoxylated and/or propoxylated ethylenediamines, sodium or potassium hydroxides and compounds of the following formula:

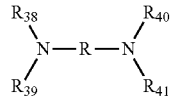

in which R is a propylene residue optionally substituted with an hydroxyl group or a $C_1$-$C_4$ alkyl radical; $R_{38}$, $R_{39}$, $R_{40}$ and $R_{41}$, identical or different, represent a hydrogen atom, a $C_1$-$C_4$ alkyl radical or $C_1$-$C_4$ hydroxyalkyl radical.

The acidifying agent can be chosen from mineral or organic acids, like hydrochloric acid, orthophosphoric acid, carboxylic acids like tartaric acid, citric acid, or lactic acid, or sulfonic acids, and the like.

The personal care/cosmetic compositions of the invention may include a physiological and cosmetically acceptable medium. Such medium may consist exclusively of water, a cosmetically acceptable solvent, or a blend of water and a cosmetically acceptable solvent, such as a lower alcohol composed of $C_1$ to $C_4$, such as ethanol, isopropanol, t-butanol, n-butanol, alkylene glycols such as propylene glycol, and glycol ethers. Alternatively, the personal care/cosmetic compositions can be anhydrous.

Generally, personal care/cosmetic compositions can be prepared by simple mixing procedures well known in the art. The invention provides a method for treating keratinous material including the skin or hair, by applying to skin or keratinous materials a personal care/cosmetic composition as described above, and then eventually rinsing it with water. Accordingly, the method makes it possible to maintain the hairstyle, treatment, care, washing, or make-up removal of the skin, the hair, and any other keratinous material. The personal care/cosmetic compositions may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process. The personal care/cosmetic compositions may also take the form of skin-washing compositions, and particularly in the form of solutions or gels for the bath or shower, or of make-up removal products. The personal care/cosmetic compositions may also be in the form of aqueous or hydro-alcoholic solutions for skin and/or hair care. The personal care/cosmetic compositions described herein are useful in personal care/cosmetic products, including, but not limited to, gels, lotions, glazes, glues, mousses, sprays, fixatives, shampoos, conditioners, 2-in-1 shampoos, temporary hair dyes, semi-permanent hair dyes, permanent hair dyes, straighteners, permanent waves, relaxers, creams, putties, waxes, pomades, moisturizers, mascaras, lip balms and foam enhancers.

The invention will now be described with reference to the following non-limiting examples:

EXAMPLES

Example 1

Synthesis of m-TMI-ME Thiocarbamate and m-TMI-ME Carbamate

The process involved the following steps:

A 500-mL flask was equipped with a mechanical stirrer, condenser, nitrogen line, temperature controller and an addition funnel. A quantity of 0.6399 mole of 2-mercaptoethanol was charged to the reaction flask. Then, 20.0 mL of triethylamine and 75.0 mL of toluene were added, and the mixture was stirred at approximately 150 rpm. At this time (t=0 hour), the flask was purged with nitrogen and the reactants heated from ambient room temperature to 50° C. During this period, at t=0.5 hour, drop-wise addition of 0.6399 mole of 3-isopropenyl-α-α-dimethylbenzyl isocyanate (m-TMI) was initiated to the flask over 1 hour. The reaction temperature was noted to increase to about 70° C. during this addition period due to the exothermic reaction. Then, at t=1.5 hours, the reactants were heated to 78° C. over 30 minutes. Later, at t=3.0 hours, the reactants were cooled to 70° C. over 30 minutes. Toluene and triethylamine were removed from the flask at t=3.5 hours using a rotary evaporator at 70° C.

Examples 2-4

Example 1 was repeated three additional times. Table 1 depicts results of these syntheses.

TABLE 1

Results of reaction of m-TMI with 2-mercaptoethanol according to Examples 1-4

| | Yield (%) | |
|---|---|---|
| Example | m-TMI-ME thiocarbamate | m-TMI-ME carbamate |
| 1 | 85% | 15% |
| 2 | 87% | 13% |
| 3 | 85% | 15% |
| 4 | 91% | 9% |

Example 5

Synthesis of poly(98.6% VP-1.4% m-TMI-ME)

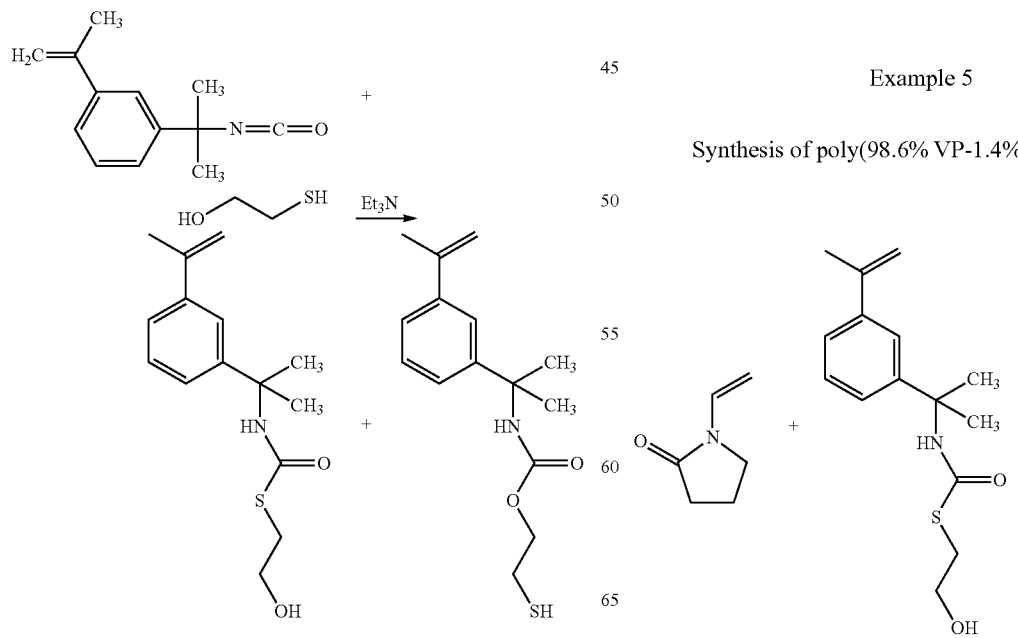

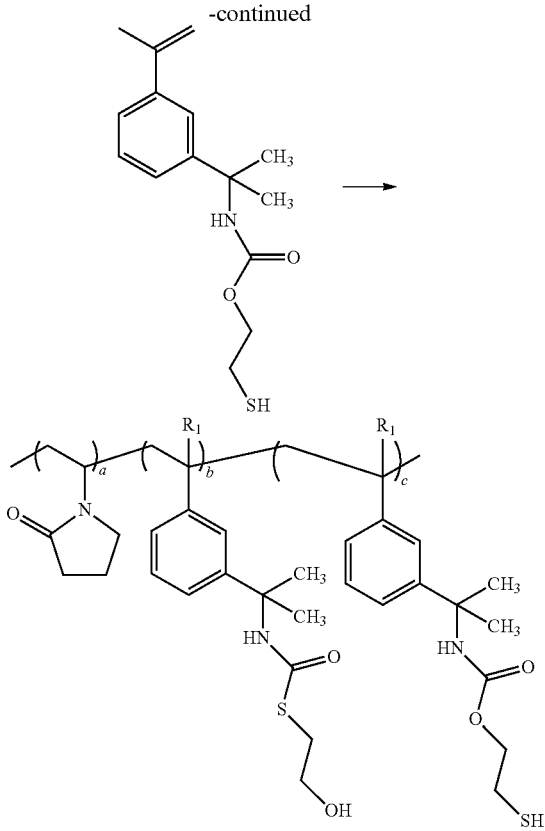

N-vinyl-2-pyrrolidone (VP) and m-TMI-ME carbamate-thiocarbamate (produced in Example 1) in a 98.6:1.4 molar ratio were copolymerized in 2-propanol (IPA). The procedure involved the following steps: First, a 0.5-L, four-neck kettle was equipped with nitrogen purge, condenser, mechanical stirrer, and an oil bath. A monomer solution was prepared by dissolving 5.0 g of m-TMI-ME (from Example 1) in 95.0 g of high purity N-vinyl-2-pyrolidone. Next, 160.0 g of IPA were added to the reaction kettle, and nitrogen purging was initiated and the flask contents heated to 65° C. Then, at t=0 hour, a first charge of 0.2 g of the initiator tert-butylperoxypivalate (Trigonox® 25-C75, Akzo Nobel) dissolved in 10.0 g of IPA was added to the reaction kettle. At this time, the monomer solution was introduced into the reaction kettle, the addition completed in one hour. Then, at t=1 hour, a second charge of 0.2 g the initiator in 10.0 g IPA was added to the reaction flask, and the conditions then held for one hour. At t=2 hours a third charge of 0.2 g of the initiator in 10.0 g of IPA was added, and the conditions then held for two hours. At t=4 hours, a charge of 0.4 g of the initiator in 10.0 g of IPA was added, and the conditions then held for two hours, and the temperature was increased to 75° C. Later, at t=6 hours, a charge of 0.1 g of the initiator dissolved in 1.0 g of IPA was added, and the reaction conditions held for one hour. This final step was repeated 12 times. Finally, after a total of 18 hours reaction time, a clear polymer was discharged from the reaction flask.

Examples 6-8

Example 5 was repeated three additional times.

Table 2 provides the results of the polymerization reaction according to Examples 5-8. The physicochemical properties of poly(VP/m-TMI-ME carbamate-thiocarbamate) are provided in Table 3.

TABLE 2

Results of poly(VP-m-TMI-ME carbamate-thiocarbamate)

| Example | HPLC (ppm) VP | HPLC (ppm) m-TMI-ME | GC (ppm) VP | R-viscosity | K-value | MW† (Da) |
|---|---|---|---|---|---|---|
| 5 | 2.8 | <0.1 | 101 | 1.32 | 34.8 | 88,800 |
| 6 | 11.7 | <0.1 | 650 | 1.23 | 29.1 | 52,200 |
| 7 | 8.0 | <0.1 | 202 | 1.27 | 31.9 | 68,900 |
| 8 | 34 | <0.1 | 57 | 1.24 | 29.8 | 57,500 |

†Based on the K-value, and relates to the viscosity-average molecular weight.

TABLE 3

Physicochemical properties of poly (VP-co-m-TMI-ME carbamate-thiocarbamate)

| Property | value |
|---|---|
| glass transition temperature (by DSC) | 156° C. |
| decomposition temperature (by TGA) | 410° C. |
| pH, 5% solids in water | 4.06 |
| turbidity, 5% solids in water | 2,613 NTU |
| turbidity, 5% solids in IPA | 2.5 NTU |
| solubility (water) | very cloudy |
| solubility (ethanol) | soluble |
| solubility (N-methyl pyrrolidone) | soluble |
| solubility (hexane) | insoluble |

Example 9

Polymerization of poly(76% VP-23% DMAEMA-1% m-TMI-ME carbamate/thiocarbamate)

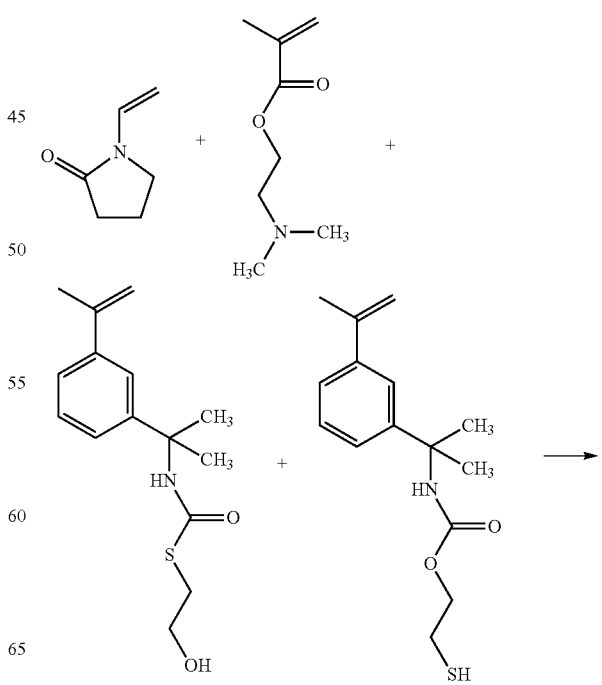

-continued

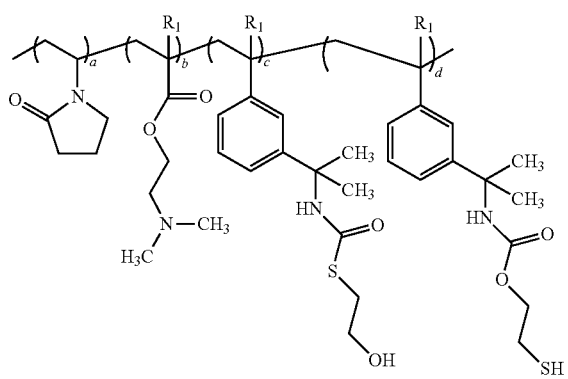

A 0.5-L, four-neck reaction kettle was equipped with a nitrogen line, a condenser, mechanical stirrer, and an oil bath. A monomer solution was prepared having 5.0 g of m-TMI-ME carbamate/thiocarbamate dissolved in 76.0 g of N-vinyl-2-pyrrolidone and 19.0 g of dimethylaminoethylmethacrylate (DMAEMA). Then, 160.0 g of 2-propanol (IPA) was added to the reaction kettle, which was purged with nitrogen, and heated to 65° C. with stirring at 200 rpm over half an hour. At t=0 hour, 0.2 g of the initiator tert-butylperoxypivalate (Trigonox® 25-C75, Akzo Nobel) was dissolved in 10.0 g of IPA and added to the reaction kettle. At this time the monomer solution was added to the reaction kettle, which was completed over the course of 1 hour. Then, at every hour at t=1 and 2 hours, 0.2 g of the initiator dissolved in 10.0 g IPA was added to the reaction kettle, which was then held for one hour. At t=4 hours, 0.4 g of the initiator dissolved in 10.0 g IPA was added to the reaction kettle. The reaction temperature increased to 75° C. and held for two hours. At every hour from t=6 to 11 hours, 0.1 g initiator dissolved in 1.0 g IPA was added to the reaction, and held for one hour. At t=12 hours, the solvent was exchanged to 200.0 g of deionized water, which was completed over the course of one hour. Meanwhile, three redox system initiators solutions were prepared. Solution A was a 72.0 g aqueous solution of 0.01% ferrous ammonium sulfate. Solution B contained 2.52 g of sodium metabisulfite in 36.0 g of deionized water. Solution C contained 3.78 g of tert-butyl hydroperoxide (70% solution in water, Sigma Aldrich) in 18.0 g of deionized water. These solutions were added from t=13 to 13 hours, when 12.0 g of solution A were added over 10 seconds, and the reaction held for 3 minutes. Then, add 6.42 g of solution B were added over 10 seconds, and the reaction held for 3 minutes. After that, 3.63 g of solution C were added over seconds, and the reaction held for 3 minutes. Finally, at t=24 hours, the reaction was terminated, and the reaction vessel contents were discharged.

Examples 10-11

Example 9 was repeated two additional times. The results of these polymerizations are summarized in Table 4. The physicochemical properties of this polymer are provided in Table 5.

TABLE 4

Results of polymerization of VP, DMAEMA and m-TMI-ME carbamate/thiocarbamate

| | HPLC (ppm) | | | GC (ppm) | | relative | | MW† |
| --- | --- | --- | --- | --- | --- | --- | --- | --- |
| Ex. | VP | DMAEMA | m-TMI | VP | DMAEMA | viscosity | K-value | (Da) |
| 9 | <4 | 0.6 | <0.1 | 55 | <LLOQ* | 1.20 | 27.0 | 42,700 |
| 10 | <4 | 71 | <0.1 | 90 | <LLOQ* | 1.20 | 27.0 | 42,700 |
| 11 | <4 | <0.3 | <0.1 | 60 | <LLOQ* | 1.18 | 25.4 | 34,400 |

*Less than the lower limit of quantitation
†Based on the K-value, and relates to the viscosity-average molecular weight.

TABLE 5

Physicochemical properties of poly (VP-DMAEMA-m-TMI-ME carbamate/thiocarbamate)

| Property | Value |
| --- | --- |
| glass transition temperature (by DSC) | 122° C. |
| decomposition temperature | 409° C. |
| pH, 5% solids in water | 8.34 |
| turbidity, 5% solids in water | 32.40 NTU |

Example 12

Synthesis of poly(62.5% VP-32.6% AA-3.6% LM-1.3% m-TMI-ME carbamate-thiocarbamate)

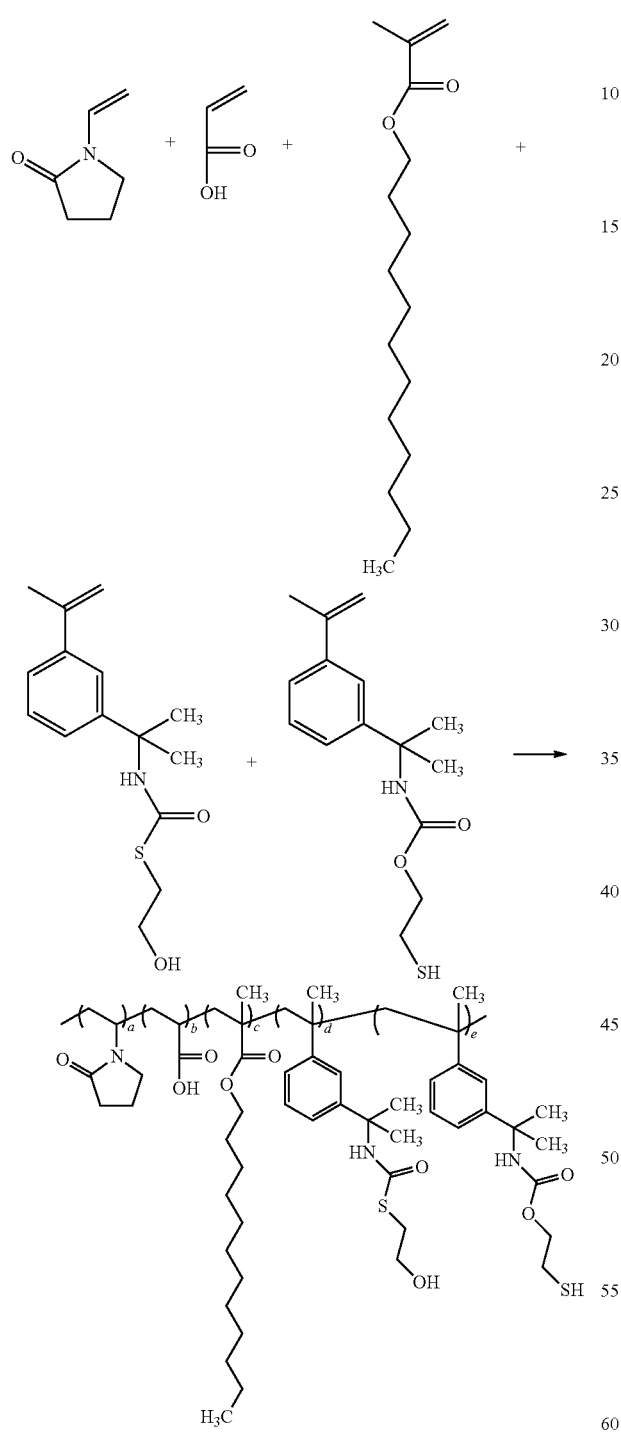

The polymerization of N-vinyl-2-pyrrolidone (VP), acrylic acid (AA), lauryl methacrylate (LM), and m-TMI-ME carbamate-thiocarbamate (produced in Example 1) in 62.5:32.6:3.6:1.3 molar ratio involved the following steps. A 0.5-L, four-neck reaction kettle was equipped with a nitrogen purge, a condenser, a mechanical stirrer, and an oil bath. A monomer solution was prepared containing 5.0 g of m-TMI-ME carbamate-thiocarbamate (from Example 1) dissolved in 68.0 g of N-vinyl-2-pyrrolidone and 9.0 g of lauryl methacrylate. Then, 500.0 g of heptane was added to the reaction vessel, stirring was started, the vessel was purged with nitrogen and heated to 65° C. over the course of 30 minutes. At t=0, 260.0 μL of the initiator tert-butylperoxypivalate (Trigonox® 25-C75, Akzo Nobel) were charged into the reaction kettle. Simultaneously, the monomer solution was fed to the kettle, and was completed in the course of 4 hours. At t=4 hours, the temperature was raised to 85° C., and held for one hour. Then, at t=5 hours, a charge of 100.0 μL of the initiator was added to the kettle. At t=6 hours, the contents of the kettle were transferred to a high-pressure steel reactor, and 0.2 g of 2,5-dimethyl-2,5-di(tert-butylperoxy)hexane (Luperox® 101, Arkema) were charged. The reactor was heated to 130° C., and maintained for 10 hours. Then, the reactor was cooled and a white polymer was discharged that when dried yielded a fine, off-white polymer powder.

NMR analysis confirmed the identity of the polymer. The residual monomer concentrations were measured by HPLC and found to be as follows: N-vinyl-2-pyrrolidone: 18 ppm, acrylic acid: 126 ppm, lauryl methacrylate: <235 ppm, m-TMI-ME carbamate-thiocarbamate: 224 ppm. The glass transition temperature of the polymer was 196° C., and the thermal decomposition temperature was 387° C. The Brookfield viscosity of a 5% (w/w) solution of the polymer in water at 10 rpm (spindle 6) was 52,000 cP.

Examples 13-15

Example 12 was repeated three additional times.

Table 6 provides the results of the polymerization reaction according to Examples 13-15.

TABLE 6

Results of poly(VP-AA-LM-m-TMI-ME carbamate-thiocarbmate)

| | HPLC (ppm) | | | | GC (ppm) | |
|---|---|---|---|---|---|---|
| Example | VP | AA | LM | m-TMI-ME | VP | AA |
| 12 | 1,700 | 260 | <235 | 130 | 2,851 | 211 |
| 13 | 466 | 270 | <235 | 103 | 1,1,73 | 250 |
| 14 | 4,000 | 780 | <235 | 182 | 6,071 | 547 |
| 15 | 18 | 126 | <235 | 224 | 112 | 99 |

Example 16

Synthesis of poly(82% VP-17% DMAPMA-1% m-TMI-ME)

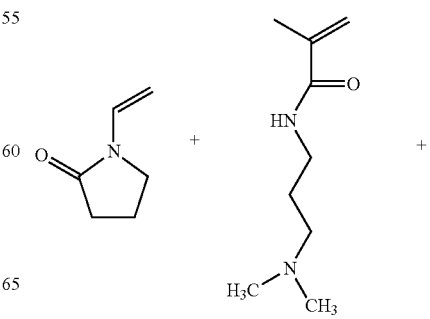

-continued

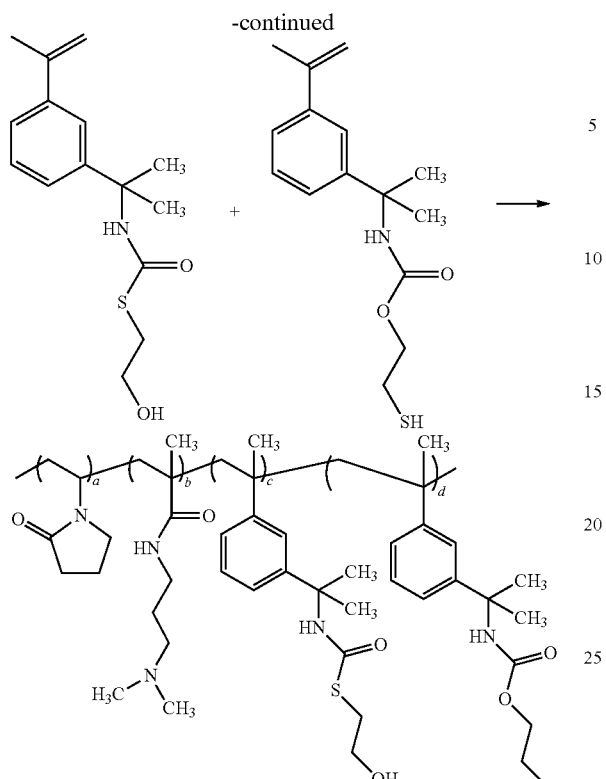

The polymerization of N-vinyl-2-pyrrolidone (VP), dimethylaminopropyl methacrylamide (DMAPMA), and m-TMI-ME carbamate-thiocarbamate (produced in Example 1) in 82:17:1 molar ratio involved the following steps: A 0.5-L, four-neck reaction kettle was equipped with a nitrogen purge, a condenser, a mechanical stirrer, and an oil bath. A monomer solution was prepared by dissolving 5.0 g of m-TMI-ME carbamate-thiocarbamate (from Example 1) in 76.0 g of N-vinyl-2-pyrrolidone and 19.0 g of DMAPMA. Then, 160.0 g of 2-propanol (IPA) was added to the reaction vessel, stirring was started, the vessel was purged with nitrogen and heated to 65° C. over the course of 1 hour. At t=0, 0.2 g of the initiator tert-butylperoxypivalate (Trigonox® 25-C75, Akzo Nobel) dissolved in 10.0 g of IPA were charged into the reaction kettle. Simultaneously, the monomer solution was fed to the kettle, and was completed in the course of 1 hour. At t=1 hour, 0.2 g of the initiator was dissolved in 10.0 g of IPA and added to the reaction kettle, which was held for 1 hour. At t=2 hours, 0.2 g of the initiator was dissolved in 10.0 g of IPA and added to the reaction kettle, which was held for 2 hours. At t=4 hours, 0.4 g of the initiator was dissolved in 10.0 g of IPA and added to the reaction kettle, which was held for 2 hours. Then, starting at t=6 hours, 0.1 g of the intiator dissolved in 1.0 g of IPA was added to the reactor and held for 1 hour. This step was repeated 6 times. Afterward, at t=12 hours, the solvent was exchanged with 200.0 g of deionized water, completed over 1 hour. Simultaneously, three redox system initiator solutions were prepared. Solution A contained 0.01 g of ferrous ammonium sulfate dissolved in 99.99 g of deionized water. Solution B contained 2.52 g of sodium metabisulfite dissolved in 36 g of deionized water. Solution C contained 3.78 g of tert-butyl hydroperoxide 70 (Brand name, manufacturer) dissolved in 18.0 g of deionized water. From t=13 to 24 hours, a charge of 12.0 g of Solution A was added over 10 seconds and then reaction conditions held for 10 minutes. Then, 6.42 g of Solution B were added over 10 seconds, and held for 10 minutes. Finally, 3.63 g of Solution C were added over 10 seconds. At t=24 hours the reaction was stopped and the contents of the kettle were discharged.

The invention has been described in detail with particular reference to various embodiments thereof, but it will be understood that variations and modifications can be effected within the spirit and scope of the invention.

What is claimed is:
1. A polymer represented by one of the structures:

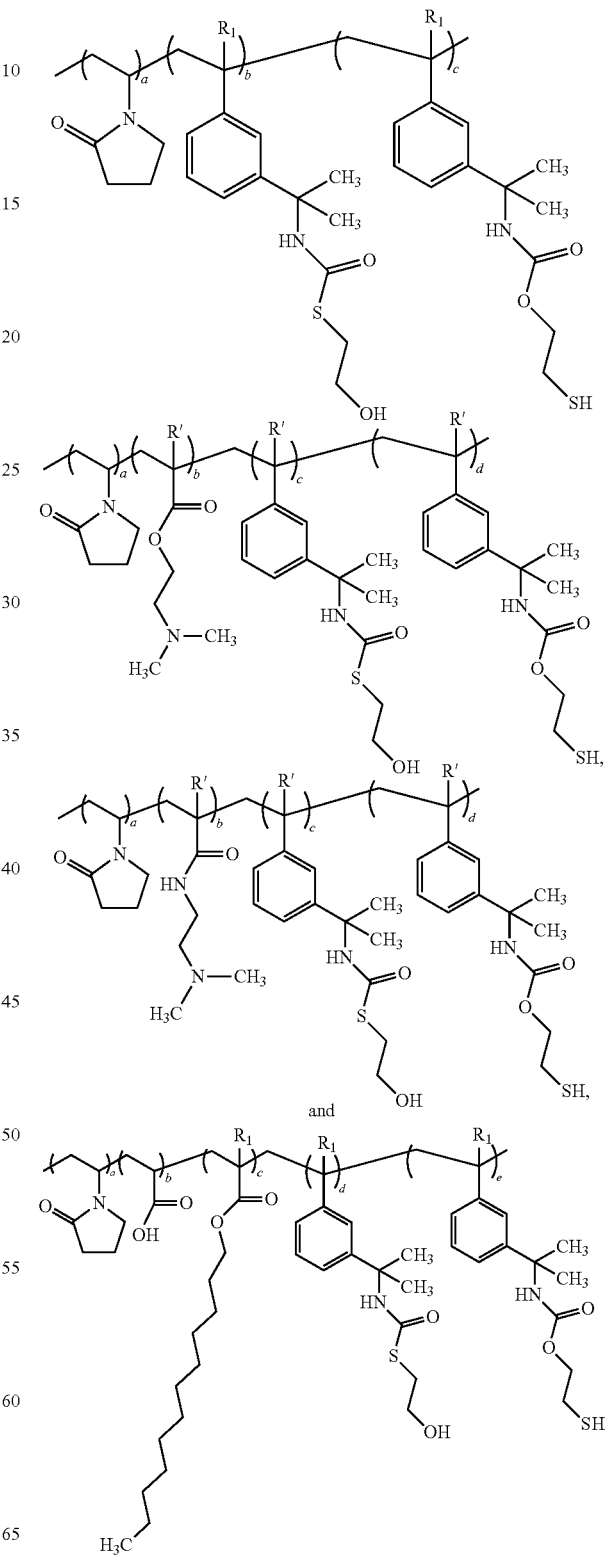

wherein $R_1$ is hydrogen or methyl; a, b, c, d, and e are molar percentages, wherein each molar percentage ranges from 0.001 mole percent to about 99.999 mole percent, and wherein the sum of the molar percentages is 100 mole percent.
2. A composition comprising a polymer represented by one of the structures:
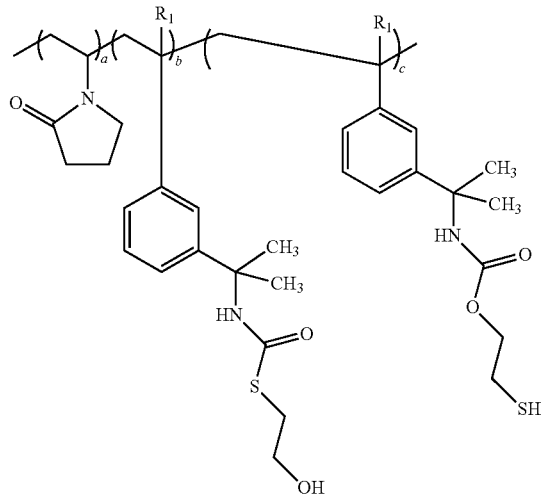
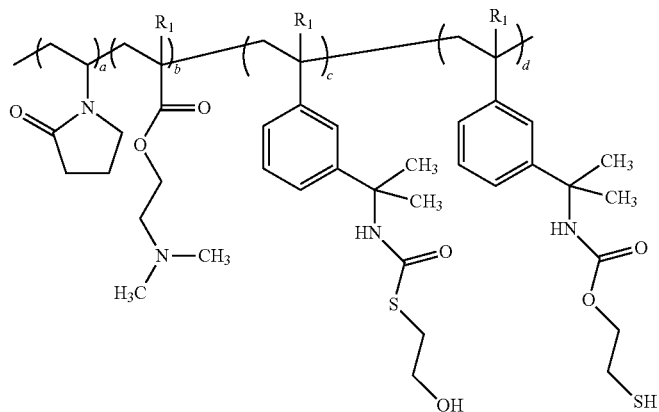
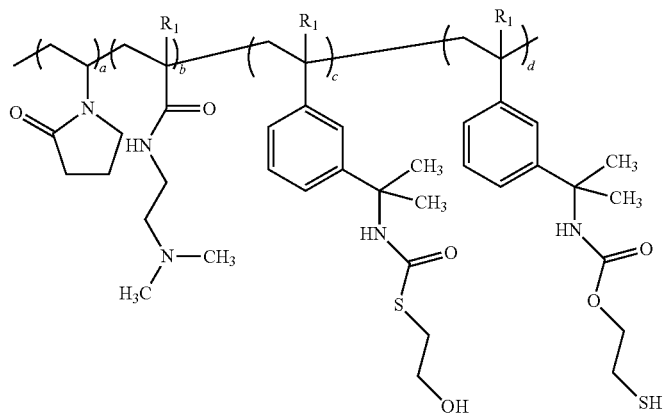
and -continued
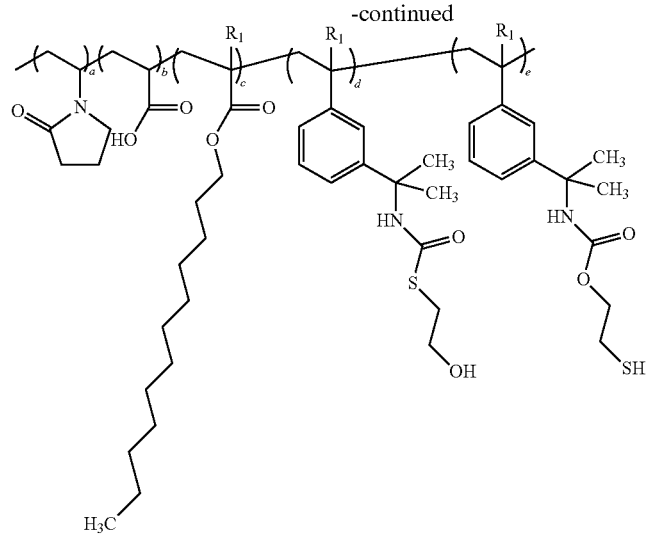
wherein $R_1$ is hydrogen or methyl; a, b, c, d, and e are molar percentages; wherein each molar percentage ranges from 0.001 mole percent to about 99.999 mole percent, and wherein the sum of the molar percentages is 100 mole percent.
* * * * *